(12) United States Patent
Alon et al.

(10) Patent No.: US 9,874,522 B2
(45) Date of Patent: Jan. 23, 2018

(54) SYSTEM FOR A STIMULATED RAMAN SCATTERING (SRS) SPECTROPHOTOMETER AND A METHOD OF USE THEREOF

(71) Applicant: OPTIQGAIN LTD., Shahar (IL)

(72) Inventors: Ram Alon, Nir Banim (IL); Dan Leigh, Jerusalem (IL); Nitzan Eliyahu, Shahar (IL); Yaron Lapidot, Givat Ada (IL)

(73) Assignee: OPTIQGAIN LTD., Shahar (IL)

( * ) Notice: Subject to any disclaimer, the term of this patent is extended or adjusted under 35 U.S.C. 154(b) by 0 days.

(21) Appl. No.: 15/128,111

(22) PCT Filed: Mar. 23, 2015

(86) PCT No.: PCT/IL2015/050301
§ 371 (c)(1),
(2) Date: Sep. 22, 2016

(87) PCT Pub. No.: WO2015/145429
PCT Pub. Date: Oct. 1, 2015

(65) Prior Publication Data
US 2017/0122874 A1    May 4, 2017

Related U.S. Application Data

(60) Provisional application No. 61/969,300, filed on Mar. 24, 2014.

(51) Int. Cl.
*G01J 3/44* (2006.01)
*G01N 21/65* (2006.01)
*G01J 3/10* (2006.01)

(52) U.S. Cl.
CPC .............. *G01N 21/65* (2013.01); *G01J 3/10* (2013.01); *G01J 3/4412* (2013.01); *G01J 2003/102* (2013.01); *G01N 2021/655* (2013.01); *G01N 2201/06113* (2013.01)

(58) Field of Classification Search
CPC ........ G01J 3/02; G01J 3/50; G01J 3/51; G01J 3/44; G01N 21/57; G01N 21/27; G01N 21/65
See application file for complete search history.

(56) References Cited

U.S. PATENT DOCUMENTS

2014/0218726 A1*  8/2014  Cheng .................... G01N 21/65
                                                               356/301

FOREIGN PATENT DOCUMENTS

| EP | 2597438 A1 | 5/2013 |
| WO | 2013110023 A1 | 7/2013 |

* cited by examiner

Primary Examiner — Abdullahi Nur
(74) Attorney, Agent, or Firm — JMB Davis Ben-David

(57) ABSTRACT

A small size, robust stimulated Raman scattering (SRS) spectrophotometer system for industrial, medical and field use, exhibiting high SNR, high resolution and very short acquisition times. The architecture of the system allowing for such features comprises three main elements: (1). Use of a narrow range tunable pump laser and an array of fixed wavelength lasers to produce the wavelength differences as required to generate the SRS (Raman) spectrum; (2). Application of analog signal processing, prior to the digital conversion, in order to obtain higher resolution and SNR; (3). Use of relatively inaccurate or unstable laser sources coupled to calibration samples, followed by various calibration methods to compensate for system instabilities, such as wavelength drift, laser inaccuracies, and variations in the optical components/elements of the system.

18 Claims, 12 Drawing Sheets

Laser sources subsystem

SYSTEM FOR A STIMULATED RAMAN SCATTERING (SRS) SPECTROPHOTOMETER AND A METHOD OF USE THEREOF

CROSS REFERENCE TO RELATED APPLICATIONS

This is the U.S. National Stage of International Application No. PCT/IL2015/050301, filed Mar. 23, 2015, which was published in English under PCT Article 21(2), which in turn claims the benefit of U.S. Provisional Application 61/969,300, filed Mar. 24, 2014.

FIELD OF THE INVENTION

The present invention relates to a stimulated Raman scattering (SRS) spectrophotometer system, its subsystems, and a method for use thereof.

BACKGROUND OF THE INVENTION

Raman spectroscopy is a very powerful tool for chemical and biochemical analysis. However, as is well known, spontaneous Raman transition spectrophotometry provides very weak signals that require long data acquisition times and high power lasers. Its performance is limited when low concentration target samples are being analyzed.

Stimulated Raman scattering (SRS) spectroscopy is an advanced spectroscopic technique, based on the Raman phenomena, useful to probe, "fingerprint" and quantitatively determine the concentration of target molecules. SRS amplifies the Raman phenomena by activating two monochromatic laser beams on a sample being investigated, a Stokes laser beam with intensity $I_s$ and a pump laser beam with intensity $I_p$. When the frequency difference of the two beams $\Delta\omega = \omega_p - \omega_s = \Omega$ ($\omega_p$ and $\omega_s$ signifying the pump beam and Stokes beam frequencies, respectively) matches the natural frequency of vibration of a target molecule $\Omega$ or vibrational-rotational mode of a target molecule, stimulated excitation of a Raman mode transition occurs in the target molecule. Stimulated Raman scattering (SRS) spectroscopy provides very good performance with short acquisition times and low average power.

When the condition $\Omega = \Delta\omega$ is met, the intensity of the pump field experiences a loss $\Delta I_p$ (SRL) while the Stokes field experiences a gain $\Delta I_s$ (SRG). The gain changes of the Raman scattering process of the beams (SRL or SRG) are proportional to the quantity of the target molecule in the sample. In a small signal regime—when the intensity of SRG or SRL is small, i.e., $\Delta I/I \ll 1$, $\Delta I_s$ and $\Delta I_p$, are described by:

$$\Delta I_s \propto N \times \sigma\text{Raman} \times I_p \times I_s \qquad [\text{Eq 1}]$$

$$\Delta I_p \propto -N \times \sigma\text{Raman} \times I_p \times I_s \qquad [\text{Eq 2}]$$

where $\Delta I$ refers to the change in intensity I of the pump and Stokes laser beams, $\Delta I_p$ and $\Delta I_s$ respectively, where I is the intensity of the pump and Stokes laser beams $I_p$, and $I_s$, respectively; N is the number of molecules in the probed/tested volume, and σRaman is the molecular Raman scattering cross-section.

In order to achieve high resolution molecular measurements where the number of molecules in the probed volume is very low, it is clear from Eq. 1 that $I_p \times I_s$ should be very high, i.e. the irradiances (intensities) (W/cm$^2$) of the pump and the Stokes laser, $I_p$ and $I_s$ respectively, should be very high. However, the noise in the system is also proportional to $I_p \times I_s$. Therefore, in cases of very low concentration where $\Delta I \lll I$, the signal to noise ratio (SNR) denoted by $\Delta I/n$ (n being noise) is very low.

From the above, it is readily understood by persons skilled in the art that the challenges that must be dealt with when using a SRS spectrophotometer system in the low concentration regime are low signal to noise ratio (SNR) and poor analog-to-digital conversion, i.e., the measured signal (I) may be high while the relevant signal ($\Delta I$) is very low.

As noted above, in the SRS technique, the gain of Raman scattering is proportional to the electro-optical field amplitude of the pump and the Stokes beams. In addition, the results are highly dependent on the accuracy of the wavelength difference of the beams. In order to achieve high resolution spectral measurement of target materials (i. e. target molecules), prior art SRS spectroscopy systems use high peak power, and femtosecond and/or picosecond lasers. When laser intensity is low, the beam diameter is reduced to maintain a minimum of about 10 MW/cm$^2$ needed for each SRS laser beam. Wide range tunable lasers are used to acquire a wide range Raman spectrum. A high level of wavelength and amplitude stabilization is required. In addition, very fast, high resolution photodetectors and real time noise reduction techniques have been used.

All this leads to very complicated implementation, which is suitable only for university laboratories and research institutes.

SRS is typically implemented in the near infra-red (NIR) region of the electromagnetic spectrum (600-1000 nm) where other physical spectrometric phenomena, e.g., fluorescence, have low expression and the molecular Raman scattering cross-section (σRaman) is high. These two factors result in a high "built-in" signal-to-noise ratio. Of particular importance is water ($H_2O$) which is present in most materials and has virtually no fluorescence in the NIR region indicated above.

Current solutions for managing the low SNR and poor resolution of SRS systems require using high peak power, narrow spectral emission widths, very accurate and stable (low noise) optical components (laser sources, photodiodes, etc.) and high resolution, low noise analog-to-digital converters (ADCs). However, these components are expensive and in many cases must be custom made. Moreover, the system's architecture is overly complicated, bulky, relatively delicate, and difficult to align and maintain alignment. It also does not allow for outdoor use. Alternatively, there are lasers which are less accurate, inherently unstable, express high background, subject to wavelength drift, and are hereby defined as unstable and possessing large impairment. Devising a method of using such unstable lasers in SRS could significantly lower cost, instrument size and increase system robustness.

Definitions

Target sample—the sample being analyzed which includes the material or materials to be identified and/or quantified. The target sample may be of any phase (plasma, gas, liquid or solid). The target sample may contain only the material(s) being identified and/or quantified or a mixture of materials and phases only some of which may be analyzed. A non-limiting example of such a mixture may include an organic compound being analyzed while dissolved in a solvent which is not analyzed. When more than one target sample is used, the series of target samples may reflect different target materials or concentrations thereof, as for example, different constituents in various chromatographic eluates or fractions leaving the chromatographic system over time or differing gases or concentrations of gases produced in a production process over time. The "target sample" at times may also be denoted herein as a "test sample" with no intent at distinguishing between the terms. The material being analyzed is usually denoted as "target material(s)" but may also be denoted by "test material(s)", "target molecules" or "target species" without any intention at distinguishing between these terms. The material(s) being analyzed may also be denoted herein as an "analyte(s)".

Reference sample—a sample that does not include the material(s) being identified and/or quantified. It may contain a part of the material mixture of the target sample which is not being identified and/or quantified or it may be empty entirely or it may contain a material not part of the target sample.

Calibration sample—A sample where the material or material(s) to be identified are known material(s) of known quantity used for calibrating the system's hardware and/or acquired data. This sample is used when a calibration method such as the one described below is employed. Use of calibration methods on the target sample data collected with the systems and methods described herein may not always be employed or even needed. These materials may also be denoted as "calibration materials" without any intention at distinguishing between these terms. The "calibration materials" may be, at times, the "target material(s)" being analyzed but need not be. The calibration sample may be considered to be a form of target sample as illumination of this sample is the same as a target sample using the same or similar detection element and detection chamber configurations. Similarly, conversion of the beam passing through the calibration sample to electronic signals and their processing is the same as that of a beam passing through a target sample.

Detection chamber (DC)—A transparent chamber specifically designed to enable SRS spectroscopy analysis of a sample. In the discussion herein, the detection chamber contains one of either a target sample, a reference sample or a calibration sample, as required. The DC may also be denoted herein as "a chamber" or "test chamber" with no intent at distinguishing between the terms.

Detection element (DE)—an enclosure containing one or more detection chambers. A DE comprising a single detection chamber holds either a target sample or a calibration sample. A DE comprising two separate detection chambers is comprised of a chamber containing either a target sample or a calibration sample as well as a chamber containing a reference sample.

Stokes laser—as used herein refers to one of the lasers in a laser array. This array will be denoted as a "Stokes laser array". Each of the lasers in the array has a wavelength/frequency different from each of the other lasers in the array and the individual wavelengths and frequencies are generally substantially fixed. They may be capable of being tunable up to ±5 nm (a much smaller range than the tunable range of the pump laser of the system) by varying the temperature of the lasers. Since the tunable range is relatively small, these lasers will be denoted herein as "non-tunable lasers" or "fixed wavelength lasers".

Stokes frequency, peak or beam—as used herein may be either the Stokes or anti-Stokes frequency, peak or beam as those terms are used in spontaneous Raman spectroscopy.

Spectrum—This is the set of intensity and wavelength digital values either measured or stored in a library. Such measured values are a representation of the Raman output values acquired from a target sample or a calibration sample. At times these values may be denoted herein as "spectral data" and "SRS spectrum" without attempting to distinguish the terms. At times the term "spectrum" may have its conventional definition when referring to a display in one form or another of the digital values in the XY plane.

Pump laser—a narrow range tunable laser enabling fast scanning of the wavelengths available in the laser's tuning range.

Real time processing—data signal processing/handling during, and in parallel to, the lasers' illumination.

Non-real time processing—processing of stored data

Error estimation—measured results of a calibration sample compared to expected results for such calibration sample thus providing a two dimensional (wavelength and intensity) error value for each point of a spectrum.

Error correction parameters—parameters for correction of the laser values for each measurement cycle based on the error estimation. These parameters are based on the most current error estimation values and on all prior error estimation values.

Adaptive calibration—a self-adjusting process that corrects its functionality according to an optimization algorithm designed to minimize a predefined error function, the input of which may be derived from acquired signals and cumulative collected data values When deviations from the above definitions are intended, such intentions will be noted, unless such deviations would be obvious to persons skilled in the art.

SUMMARY OF THE PRESENT INVENTION

It is an object of the present invention to provide a small size, robust and comparatively low cost stimulated Raman scattering (SRS) spectrophotometer system for industrial, medical and field use. The system exhibits high SNR, high resolution, a wide Raman shift spectrum and very short acquisition times. The system overcomes the above discussed performance limitations of spontaneous Raman scattering and the implementation limitations of SRS. The system uses mostly off-the-shelf, inexpensive components and is of a rugged mechanical and optical design based on fiber/integrated optics capable of being operated under field conditions. Even though off-the-shelf components are generally less stable, are "noisier" and have lower performance capabilities, the present system compensates for the disadvantages of these components by using various components and methods as described below. The system architecture of the present invention which allows for such features comprises the following main elements: (1). Use of a narrow range tunable pump laser and an array of fixed wavelength Stokes lasers to produce the wavelength differences required to generate a wide SRS (Raman) spectrum. In other embodiments, the pump laser may be an array of fixed wavelength lasers while the Stokes laser may be comprised of a tunable laser; (2). Application of analog signal processing prior to analog-to-digital conversion thereby providing higher resolution and better SNR; (3). Use of relatively inaccurate or unstable laser sources coupled to calibration samples, followed by use of at least one of various calibration methods to compensate for system instabilities, such as wavelength drift, inaccuracies of the pump and Stokes lasers, and variations in the optical components/elements of the system; (4). Use of a single laser source subsystem to serve multiple detection elements. and (5) Use of the system of the current invention for real-time control of industrial processes, through immediate response and high resolution monitoring The present invention overcomes the known technical limitations of currently available SRS spectrophotometers obviating the need for using expensive hardware, high peak power, wide tuning range tunable lasers, very accurate femtosecond or picosecond laser sources and high resolution analog-to-digital convertors (ADC). In all cases the inexpensive hardware elements discussed herein are readily purchasable from suppliers well-known to persons skilled in the art. This allows for more extensive use of the SRS phenomenon in a wider range of environments.

Another object of the present invention is to provide a high resolution, real time molecular spectrophotometric analysis system that can be integrated into other devices. Such devices can include, but are not limited to, analytical chemistry instruments, molecular diagnostic medical devices, industrial process and quality control devices, food quality monitors, environment monitors, and geochemical molecular analysis instruments.

Another object of the present invention is to provide an SRS spectrophotometer system which will require reduced data acquisition times.

It is a further object of the present invention to provide a small portable SRS spectrophotometer system which allows field use.

It is a further object of the present invention is to provide methods for operating the above system.

These and other objects, features and advantages of the present invention will become apparent in light of the detailed description of the embodiments thereof, and as illustrated in the accompanying drawings.

To achieve the above objects, in one aspect of the present invention there is provided a stimulated Raman scattering spectrophotometer (SRS) system. The system includes a pump laser and a Stokes laser wherein one of either the pump or the Stokes laser is a narrow range tunable laser while the other is a fixed wavelength laser array. The tunable and fixed wavelength lasers are adapted and configured to produce a series of combined laser beams so that only one of the fixed wavelength laser is activated at a given time and forms a combined beam with the tunable laser. There is also a timing generator activating the tunable and fixed wavelength lasers in a predetermined sequence for generating the series of combined beams. The system also includes one or more detection probes including one or more detection elements containing a target sample in optical communication with the pump and Stokes lasers so as to be illuminated by the combined beams. One or more wavelength splitters split the combined beams received from the detection elements into pump and Stokes laser beams. A plurality of photodetectors is present for receiving the split beams and for converting them into analog signals. The analog signals are then conveyed to a plurality of analog-to-digital convertors for conversion to digital signals. Finally, a control and data processing subsystem further processes the digital signals generating a SRS spectrum from the processed signals.

In one embodiment of the system of the present invention, the pump laser is a narrow range tunable laser and the Stokes laser is an array of fixed wavelength lasers. In another embodiment of the system, the wavelength of each of the lasers in the array of fixed wavelength lasers is different from the wavelength of every other laser in the array. In a further embodiment of the system, the difference in wavelengths between adjacent fixed wavelength lasers in the array is equal to or less than the narrow tunable range of the tunable laser. In still another embodiment of the system, the timing generator synchronizes activation of the fixed wavelength lasers and tunable laser so that each fixed wavelength laser forms a separate combined beam with the tunable laser at each of its tunable wavelengths and so that all combinations of their wavelength differences are generated. In yet another embodiment of the system, the tunable and fixed wavelength lasers are pulsed lasers where the tunable laser has a pulse duration of a length such that a duration of any of the fixed wavelength laser pulses falls completely within the duration of the tunable laser pulse when both are activated together. In another embodiment of the system, the timing generator activates the lasers of the fixed wavelength laser array at a repetition rate of 64-10,000 repetitions per spectral point. In a further embodiment of the system, the narrow tuning range of the tunable laser is not less than about 5 nm and not more than about 40 nm. In another embodiment of the system, each of the one or more detection probes further comprises a plurality of detection elements and further comprises a multiplexer. The multiplexer is adapted and configured to illuminate each of the plurality of detection elements independently and in a predetermined sequence with the combined beam.

In yet another embodiment of the system, the pump laser is a fixed wavelength laser array and the Stokes laser is a narrow range tunable laser. In still another embodiment of the system, the wavelength of each of the lasers in the fixed wavelength array is different from the wavelength of every other laser in the fixed wavelength array. In another embodiment of the system, the difference in wavelengths between adjacent fixed wavelength lasers in the fixed wavelength laser array is equal to or less than the narrow tunable range of the tunable laser. In yet another embodiment of the system, only one fixed wavelength laser is activated at a given time and the timing generator synchronizes activation of the tunable laser and fixed wavelength lasers so that all combinations of their wavelength differences are generated. In a further embodiment of the system, the tunable laser and fixed wavelength lasers are pulsed lasers and the tunable laser has a pulse duration of a length such that a duration of any of fixed wavelength laser pulses falls completely within the duration of the tunable laser pulse when both are activated together. In still another embodiment of the system, the timing generator activates the lasers of the fixed wavelength laser array at a repetition rate of 64-10,000 repetitions per spectrum point. In another embodiment of the system, the narrow tuning range of the tunable laser is not less than about 5 nm and not more than about 40 nm. In a further embodiment of the system, each of the one or more detection probes further comprises a plurality of detection elements and further comprises a multiplexer. The multiplexer is adapted and configured to illuminate each of the plurality of detection elements independently and in a predetermined sequence with the combined beams.

In still other embodiments of the above system there may be use of any combination of, or use of a single one of, the following characteristics or features: a. the laser array comprises between 2 and 20 lasers; b. the tunable and fixed wavelength lasers are pulsed lasers; c. the tunable and fixed wavelength pulsed lasers have pulse durations of between about 0.05 ns to about 9 ns; d. the timing generator generates a Raman spectrum with a resolution of between about 0.1 nm to about 1 nm; e. the one or more detection probe is a plurality of detection probes; and f. the tunable laser can be operated in a continuous scanning mode or in a discrete specific spectral peak mode.

In a second aspect of the invention, there is provided a stimulated Raman scattering spectrophotometer system. The system includes a laser sources subsystem including a pulsed pump laser and a pulsed Stokes laser array. One of either the pump laser or the Stokes laser array is tunable and the lasers are adapted and configured to produce a series of combined laser beams. The system also includes one or more detection elements which contain a target sample which is illuminated by the series of combined beams. The system also includes a photodetector subsystem including one or more wavelength splitters for splitting the combined beams received from the one or more detection elements. The split beams include pump and Stokes laser beams. A plurality of photodetectors is adapted and configured for receiving the split beams, converting them to analog electronic signals, and then directly providing the analog signals to a plurality of analog-to-digital convertors (ADCs). In parallel, the analog signals are also conveyed from the photodetectors to an analog processing unit (APU) which is configured and adapted to manipulate the analog signals in order to increase the signal-to-noise ratio (SNR) and improve resolution of the signal. The manipulated analog signals are then conveyed from the APU to the plurality of ADCs where all analog signals are converted to digital signals. A control and data processing subsystem includes a digital signal processor (DSP) and/or central processing unit (CPU) which receives and further processes the digital signals, generating a SRS spectrum from the processed digital signals.

In one embodiment of this system, the one or more detection elements are two detection chambers one of which contains a reference sample and the other contains a target sample.

In another embodiment of this system, the detection element further includes an intensity beam splitter. The intensity beam splitter is adapted and configured for splitting the intensity of the combined beam into a first portion and a second portion. The first portion of the split beam is directed to pass through the reference sample and the second portion of the split beam is directed to pass through the target sample.

In a further embodiment of the system, one or more photodetectors convert the pump laser beam and the Stokes laser beam of the target sample to analog signals. Two or more other photodetectors convert the pump laser beam and the Stokes laser beam of the reference sample to analog signals.

In still another embodiment of this system, the DSP and/or the CPU is adapted to receive and process the target and reference sample digital signals from the ADC. The reference sample digital signals are used as background information for the target sample digital signals. The processed reference sample digital signals are subtracted from the target sample digital signals reducing noise and further increasing resolution and enhancing SNR of the target signal.

In a further embodiment of the system, the APU comprises an analog circuit configured for real-time processing of the analog signals of associated target and reference samples in at least one detection element. The reference signal represents the background signals. The reference signal is subtracted from the target signal in the APU thus increasing resolution and enhancing SNR of the target signal.

In another embodiment of the system, the pulsed pump laser pulse duration is longer than the pulsed Stokes laser pulse duration. Therefore for a portion of the time during the pulse of the pump laser the target sample is illuminated by the pump laser without the Stokes laser illuminating the target sample. During the remainder of the pump laser pulse duration, both pump and Stokes lasers illuminate the target sample.

In still another embodiment of the system, the APU comprises an analog circuit configured for real-time processing of the analog signals. The pump signal is delayed using a delay line so that the pump signal, from the time the pump laser is illuminated while the Stokes laser is not, serves as a reference signal representing background signals. The reference signal is subtracted from the target signal thus increasing the resolution and enhancing the SNR of the target signal.

In a further embodiment of the system, the ADCs used are 8-10 bit ADCs which still maintain high resolution of the SRS data.

In another embodiment of the system, wherein the target sample in the detection element is a stream of target material(s) that is to be analyzed.

In a third aspect of the invention there is provided a stimulated Raman scattering spectrophotometer system. The system includes a laser sources subsystem comprising a pulsed pump laser and an array of pulsed Stokes lasers. One of either the pump laser or the Stokes laser array is tunable, and the lasers are adapted and configured to produce a series of combined laser beams. The system also includes one or more detection elements wherein one or more detection chambers include a target sample and one or more detection chambers include a calibration sample. The two or more detection chambers are illuminated sequentially by the series of combined laser beams. Also included in the system is one or more wavelength splitters for splitting the combined beams received from the at least two detection chambers into pump and Stokes laser beams. A plurality of photodetectors for converting the pump and Stokes laser beams into analog signals which are then converted to digital signals by ADCs are also included in the system. Finally, the system includes a control and data processing subsystem for further processing and calibrating the digital signals and generating a SRS spectrum from the processed signals.

In an embodiment of the system, the Stokes lasers and pump laser comprise unstable lasers with large impairments.

A system according to any one of the above described spectrophotometric systems can be used for real-time molecular level monitoring, real-time measurement of industrial processes, real-time feedback control of these processes, temperature measurement of industrial processes for real-time molecular level monitoring, real-time measurement of environmental parameters, and detection of biomarkers in medical applications.

In a fourth aspect of the present invention there is provided a method for improving the accuracy of a stimulated Raman scattering (SRS) spectrum of a target sample generated by a SRS spectrophotometer system defined as in the previous systems described above. The method includes the steps of:
  i. generating a SRS spectrum of the calibration sample;
  ii. estimating measurement errors by comparing the measured calibration sample spectrum with a series of spectra for different known quantities of the known calibration material(s) in the calibration sample;
  iii. if the measurement errors are equal to or exceed predefined values, calibrating the physical parameters of the laser sources and repeating step i and ii;
  iv. if the measurement errors are less than predefined values, calculating calibration parameters using the estimated measurement errors;

v. generating a SRS spectrum of one or more target sample(s);

vi. modifying the SRS spectrum of each target sample using the calibration parameters; and vii. conveying the modified target spectrum to an output device or control device for control of an operational system.

In an embodiment of the method, the step of estimating measurement errors and calculating calibration parameters includes calculating separate measurement errors and calibration parameters for each of the lasers used in the SRS spectrophotometer system.

In yet another embodiment of the method, in the step of estimating measurement errors and calculating calibration parameters, each measurement error and calibration parameter is a two-dimensional value: wavelength error/parameter and intensity error/parameter.

In a further embodiment of the method, if there is continuous or periodic SRS spectrum generation, the step of estimating measurement errors, uses a combination of current and prior estimated error measurements employing a known adaptive calibration method.

BRIEF DESCRIPTION OF THE DRAWINGS

The present invention will be understood and appreciated more fully from the following detailed description taken in conjunction with the drawings in which:

FIG. 14 is a flowchart of an embodiment of a method for the data processing required to generate the SRS spectra in the present invention; and.

Similar elements in the Figures are numbered with similar reference numerals.

DETAILED DESCRIPTION OF PREFERRED EMBODIMENTS

It should be noted that throughout this document all data is exemplary. It is used solely to present and explain the invention and as a possible implementation of the invention and is not intended to limit the invention. Similarly, the present invention has been described in relation to particular embodiments which are intended in all respects to be illustrative rather than restrictive.

As used herein "comprising" or "comprises" or variants thereof is to be interpreted as specifying the presence of the stated features, integers, steps, or components as referred to, but does not preclude the presence or addition of one or more additional features, integers, steps, components, or groups thereof. Thus, for example, a method comprising a given step may contain additional steps.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all values within the range. It is also intended to include all ranges within the upper and lower values of the endpoints of the specified range. It is not intended that the scope of the invention be limited to the specific values recited when defining a range.

The SRS spectrophotometer system of the present invention is contemplated to be capable of detecting and measuring very small traces of chemical or biochemical molecules with a sensitivity as low as $10^{-9}$-$10^{-15}$ gram. The intensity of the laser beams is intended to be very high, on the order of about 10 MW/cm$^2$ for each beam. To achieve such high intensity, the beams are focused on very small detection areas, for example, 10 μm×10 μm, and the beam pulses are of very short duration, for example, 0.001-1000 nanoseconds. Spectrum generation times typically may be on the order of 0.1-1.0 second. Without limiting the invention, a typical spectrum width may be 3500 cm$^{-1}$-4000 cm$^{-1}$ (about 210 nm to about 260 nm while the central wavelength may be in the 900 nm-950 nm range). The system described herein is contemplated to demonstrate amplification of the Raman phenomena, typical amplification being about 5 orders of magnitude.

Figure 1:
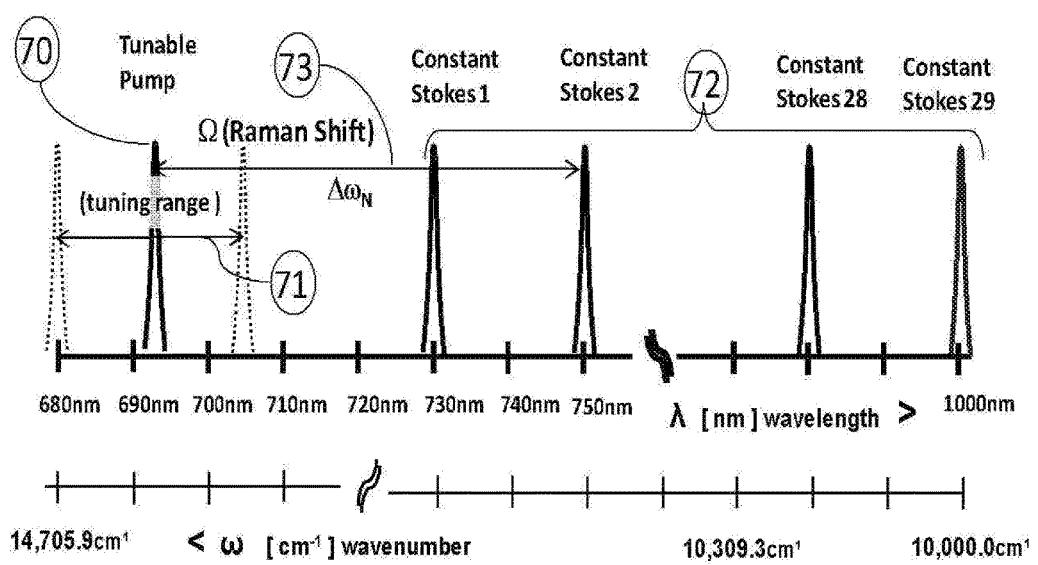
FIG. 1 is a spectrum instantiating the SRS phenomenon used in the systems of the present invention.

Reference is now made to FIG. 1, which illustrates a spectrum of a typical pump laser and Stokes laser array output in a SRS spectrophotometer system constructed and operated as described herein. It instantiates the physical phenomenon encountered when using the system. In this exemplary spectrum, the peak wavelength 70 of the tunable pump laser is centered at about 692 nm. The frequency associated with this wavelength is generally designated as $\omega_p$. The tunable wavelength range 71 of the pump laser represents the wavelength range extending from about 680 nm to about 705 nm and its associated frequency is generally denoted herein as $\Delta\omega_t$. An array of N Stokes lasers (here N is 29) is denoted in FIG. 1 as 72. Each of the lasers in array 72 is a fixed wavelength laser that falls within the range of about 730 nm to about 1000 nm.

The wavelength of each laser in the array is different from the wavelengths of each of the other lasers in the array. The laser wavelengths are chosen to span a range with the wavelength difference between two adjacent Stokes laser frequencies, $\omega_{Sn-1}$ and $\omega_{Sn}$, equal or less than the full tunable laser tuning range 71. This can be represented by $\Delta\omega_{Stokes} = \omega_{Sn-1} - \omega_{Sn} \leq \Delta\omega_t$ where $\Delta\omega_t$ is the tuning range 71 of the pump laser.

The $n^{th}$ Stokes laser has a frequency denoted as $\omega_{Sn}$. Selection of a certain fixed wavelength Stokes laser together with a certain wavelength setting of the tunable pump laser defines a frequency difference $\Delta\omega_n$ (where $\Delta\omega_n = \omega_p - \omega_{Sn}$) that is being tested. When $\Delta\omega_n = \Omega_j$ that is when $\Delta\omega_n$ matches a frequency equal to the frequency $\Omega_j$ of the jth active Raman mode vibrational frequencies of the irradiated target molecule(s), stimulated excitation of a Raman mode transition in the target molecules occurs. When $\Delta\omega_n = \Omega_j$ there is a substantial decrease of the intensity (Eq. 2) of the pump laser beam and an increase of the intensity of the Stokes laser beam (Eq. 1). While the above has been discussed in terms of vibrational Raman modes, it will be appreciated by persons skilled in the art that the discussion herein, both infra and supra, may apply equally as well to rotational Raman transitions and vibrational/rotational Raman transitions.

When $\Delta\omega_n$ is equal to a Raman vibration mode frequency $\Omega_j$ of the target material(s), the weak Raman emission becomes amplified typically up to $10^5$ in comparison to the spontaneous Raman emission intensities.

When using SRS spectrophotometer systems including the system of the present invention, both the pump and Stokes beams irradiate the target material(s) substantially simultaneously, that is they are both activated within a fraction of a picosecond to within a fraction of a microsecond of each other. When the respective frequency difference $\Delta\omega_n$ (of the pump and Stokes beam frequencies) equals $\Omega_j$ of the jth active Raman mode vibrational frequencies, energy is transferred from the pump beam (SRL) to the Stokes beam (SRG) as described previously.

In order to generate the required frequency differences $\Delta\omega_n$ to produce the SRS spectrum, the system generates all the laser pair frequency differences $\Delta\omega_n$ ranging, in the example of FIG. 1, from about 25 nm to about 320 nm (about 485 cm$^{-1}$ to about 4706 cm$^{-1}$) in FIG. 1. This is achieved by generating all the combinations of the tunable pump laser frequencies $\omega_p$ with each fixed Stokes laser frequency $\omega_{Sn}$, one by one.

The above described stimulated Raman gain (SRG) effect plus the iterative scanning at the desired frequency range as discussed below allows for easier detection of what would usually be a Raman peak of weak intensity. The discussion above is based on the numerical wavelength and corresponding frequency values shown in the spectrum of FIG. 1. It should be understood that this is only an exemplary spectrum and uses exemplary wavelengths/frequencies. It should also be readily understood by persons skilled in the art that wavelength in nanometers (nm) denoted by $\lambda$ and frequency in wavenumbers (cm$^{-1}$) generally indicated by $\omega$ will be used interchangeably as the conversion from one to the other is well known.

Implementation of the present invention can be utilized in any of a large range of spectral ranges, the choice of specific spectral range for evaluation is dictated by the target molecules to be tested.

The architecture of the system which provides for the detection advantage of the present invention includes the following main elements and/or features:

A. Use of a narrow range tunable pump laser and an array of fixed wavelength lasers to produce a wide range SRS spectrum. The laser wavelengths are chosen to span the analysis range desired. The wavelength of each of the Stokes lasers is different from every other laser in the array and the difference in frequencies between adjacent Stokes laser beam frequencies is equal to or less than the tunable pump laser tuning range. This can be represented by $\Delta\omega_{Stokes} = \omega_{Sn-1} - \omega_{Sn} \leq \Delta\omega_t$ where the tuning frequency range of the pump laser is denoted by $\Delta\omega_t$ and $s_{n-1}$ and $s_n$ indicate two Stokes lasers from the Stokes laser array emitting beams with adjacent frequencies $\omega_{Sn-1}$ and $\omega_{Sn}$, respectively.

In other embodiments of the present invention, the pump laser may be a fixed wavelength laser array while the Stokes laser array may be comprised of a single tunable laser. Such a configuration should be readily achievable by persons skilled in the art as it requires only a minimal number of changes to the first configuration described herein.

B. Application of analog signal processing prior to the analog-to-digital conversion in order to obtain higher resolution and a larger SNR. This can be achieved by using a variety of methods. For example:

1) Use of a small portion of the combined pump and Stokes laser output for measurements on a reference sample which is a representation of the beam without the SRS signal (that is it represents the "noise" of the system). Each combined beam exiting from the target sample and the reference sample is split into Stokes and pump beams. The four beams are each converted to electronic signals using four separate photodetectors, one for each beam. A portion of the output is fed into an analog processing unit (APU) in order to improve resolution and SNR.

2) Sampling the pump laser signal during an interval when the Stokes laser signal is absent. This represents the background "noise" without the SRS signal. The SRS signal (pump plus Stokes) and the delayed signal (pump only) are compared and used to improve resolution and SNR.

C. Use of relatively inaccurate or unstable laser sources coupled to calibration samples, followed by adaptive calibration methods to compensate for system instabilities, such as wavelength drift, and inaccuracies of the pump and Stokes lasers. The calibration sample is illuminated by the same pump and Stokes laser sources as in paragraphs 1) and 2) immediately above and data is obtained for estimation of system measurement errors. The measured errors are used to calibrate the system's hardware and/or acquired data, the latter using an adaptive calibration algorithm.

D. Use of a single laser sources subsystem to illuminate multiple detection elements. It is contemplated that the present invention can be applied by two system configurations. However these configurations are not to be deemed as limiting the invention. The configurations are:

i. A centralized configuration (FIG. 2) where one photodetector subsystem and one control and data processing subsystem are used to process the emitted beams from multiple detection elements. This configuration is optimal when the signal integrity of the emitted optical signal is relatively secure.

ii. A distributed configuration (FIG. 3) where a separate photodetector subsystem and a separate control and data processing subsystem are coupled to each detection element.

This configuration is optimal when significant effort is required to preserve signal integrity of the emitted optical signal.

The system of the present invention may be used in either of two modes of operation:
i) Scanning mode—in this mode the spectrum of the target material(s) is scanned over a predetermined spectral range and the system detects and measures at least one of the Raman peaks of the target material(s); or
ii) Specific spectral peak mode—in this mode, only one or more specific peaks of the one or more target materials are scanned, saving energy, reducing exposure to the laser illumination and reducing data acquisition time.

In what will be described herein only the scanning mode will be discussed. It should readily be apparent to a person skilled in the art what modifications would be needed to use the system of the present invention in the specific spectral peak mode.

Figure 2:
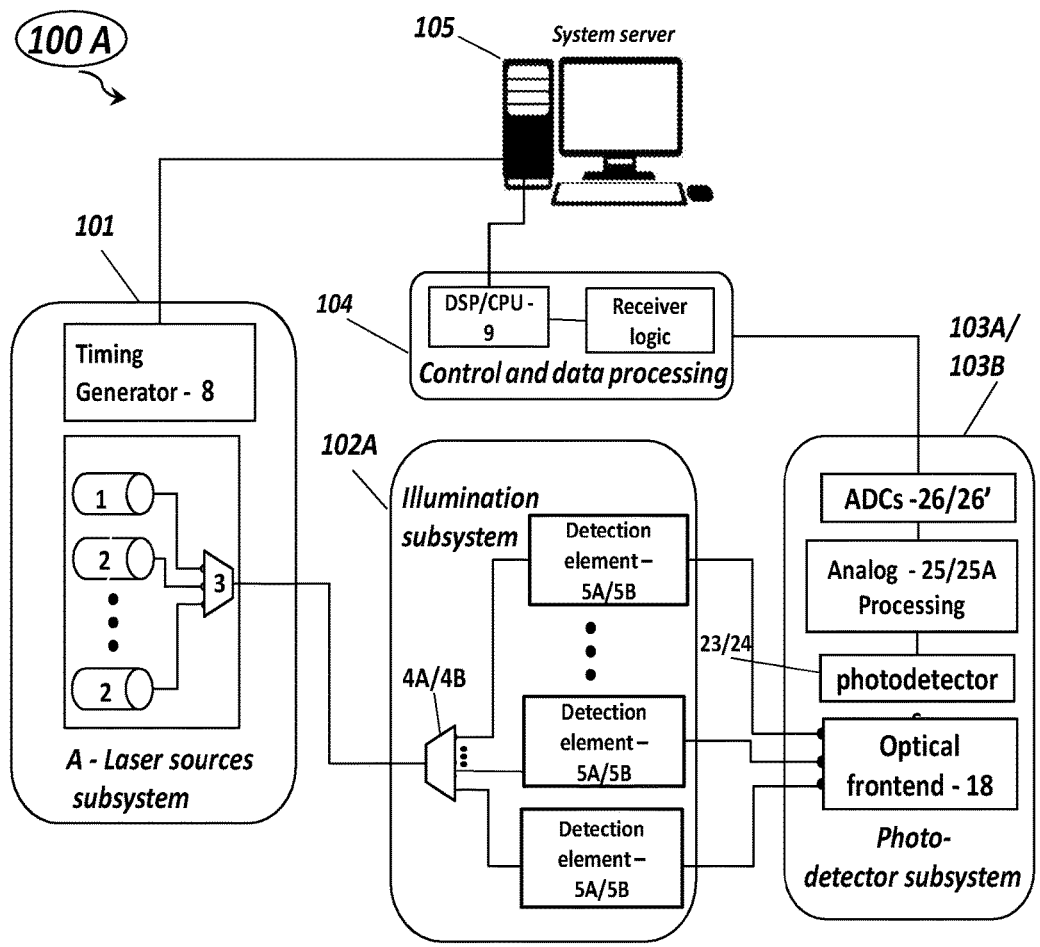
FIG. 2 is a schematic drawing of an embodiment of the SRS spectrophotometer system of the present invention in a centralized configuration.

Reference is now made to FIG. 2, a schematic drawing of an embodiment of the SRS spectrophotometer system 100A of the present invention. In this "centralized" configuration, a single photodetector subsystem and a single control and data processing are used in conjunction with one or more detection elements.

System 100A is comprised of five subsystems: a laser sources subsystem 101 (described in conjunction with FIG. 4); an illumination subsystem 102A (described in conjunction with FIG. 5); a photodetector subsystem 103 (configured as either subsystem 103A or subsystem 103B and described in detail in conjunction with FIG. 9 and FIG. 10, respectively); a control and data processing subsystem 104; and a system server 105.

Figure 3:
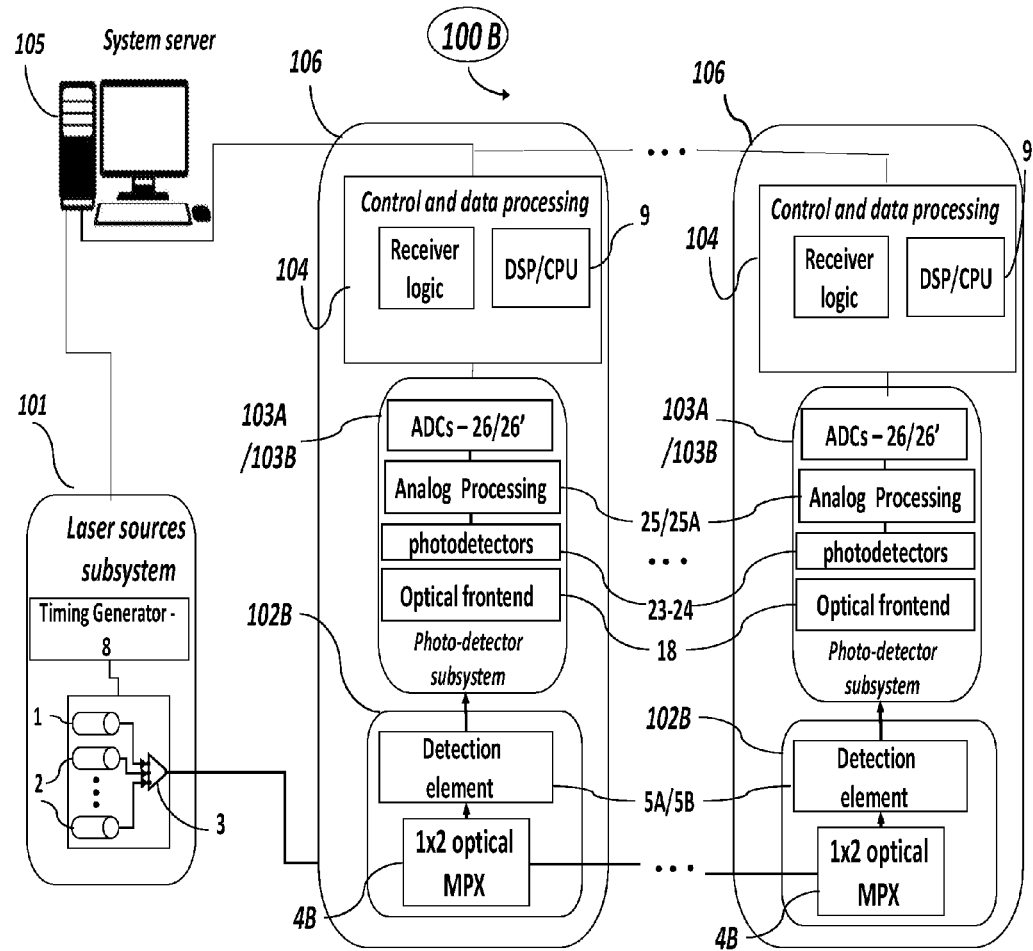
FIG. 3 is a schematic drawing of an embodiment of the SRS spectrophotometer system of the present invention in a distributed configuration.
Figure 4:
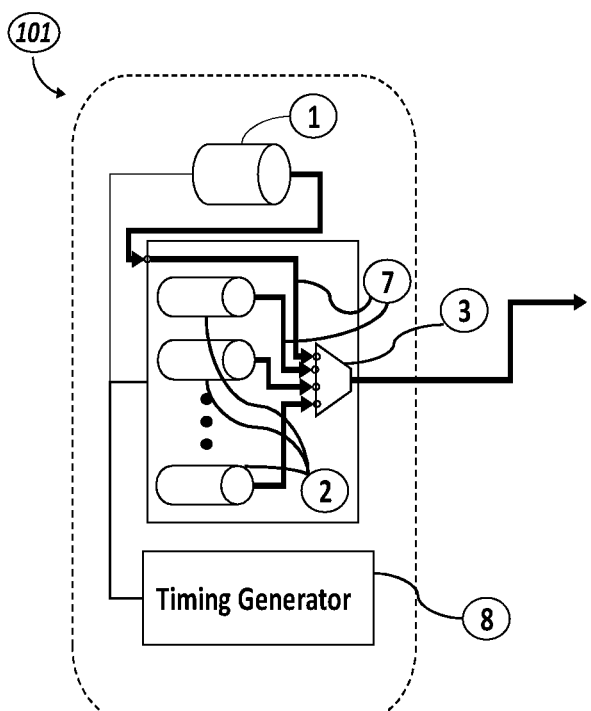
FIG. 4 is a schematic drawing of an embodiment of the laser sources subsystem used in the spectrophotometer systems of FIG. 2 or FIG. 3.

Reference is now made to FIG. 3 where system 100B is comprised of a single laser sources subsystem 101 described in detail in conjunction with FIG. 4; one or more detection probes 106; and a single system server 105.

Figure 6:
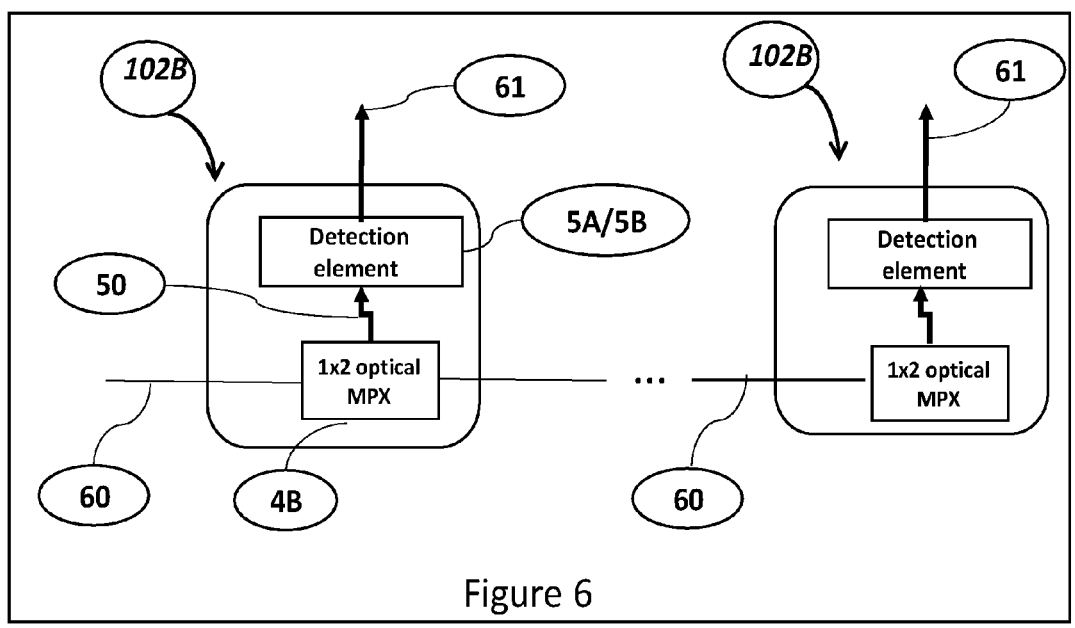
FIG. 6 is a schematic drawing of an embodiment of an illumination subsystem that may be used in the spectrophotometer system of FIG. 3.
Figure 9:
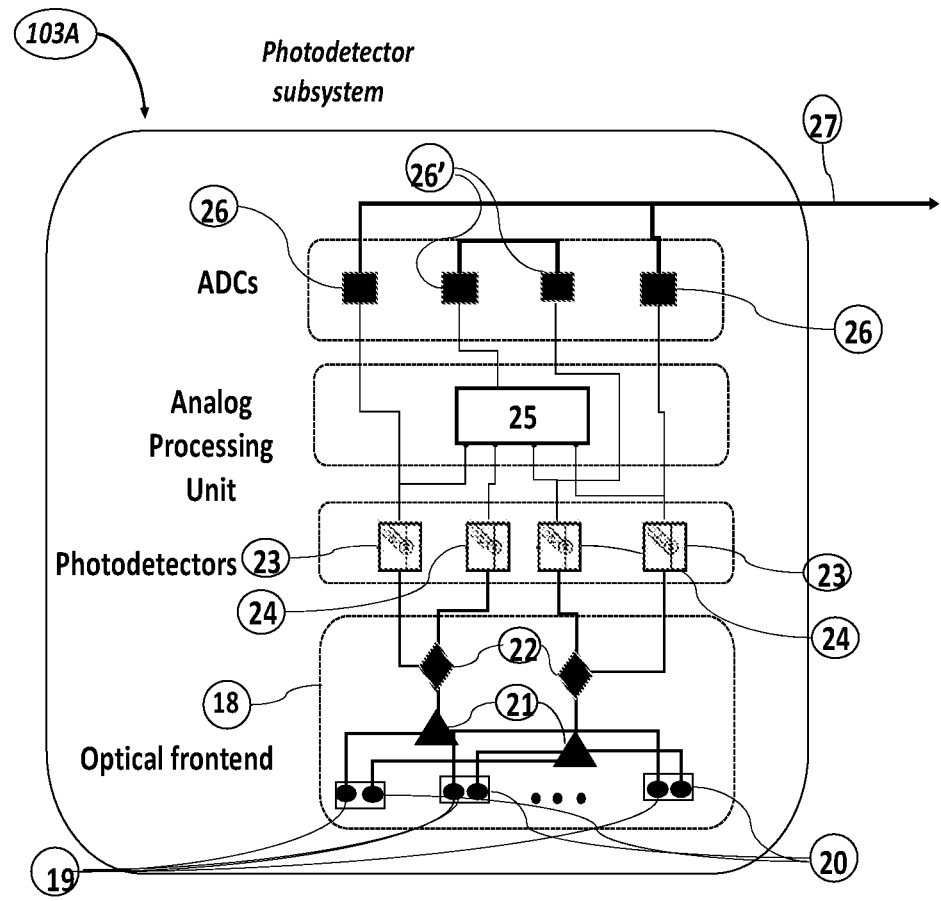
FIG. 9 is a schematic drawing of an embodiment of a photodetector subsystem when a reference sample is used for SNR and resolution improvement.
Figure 10:
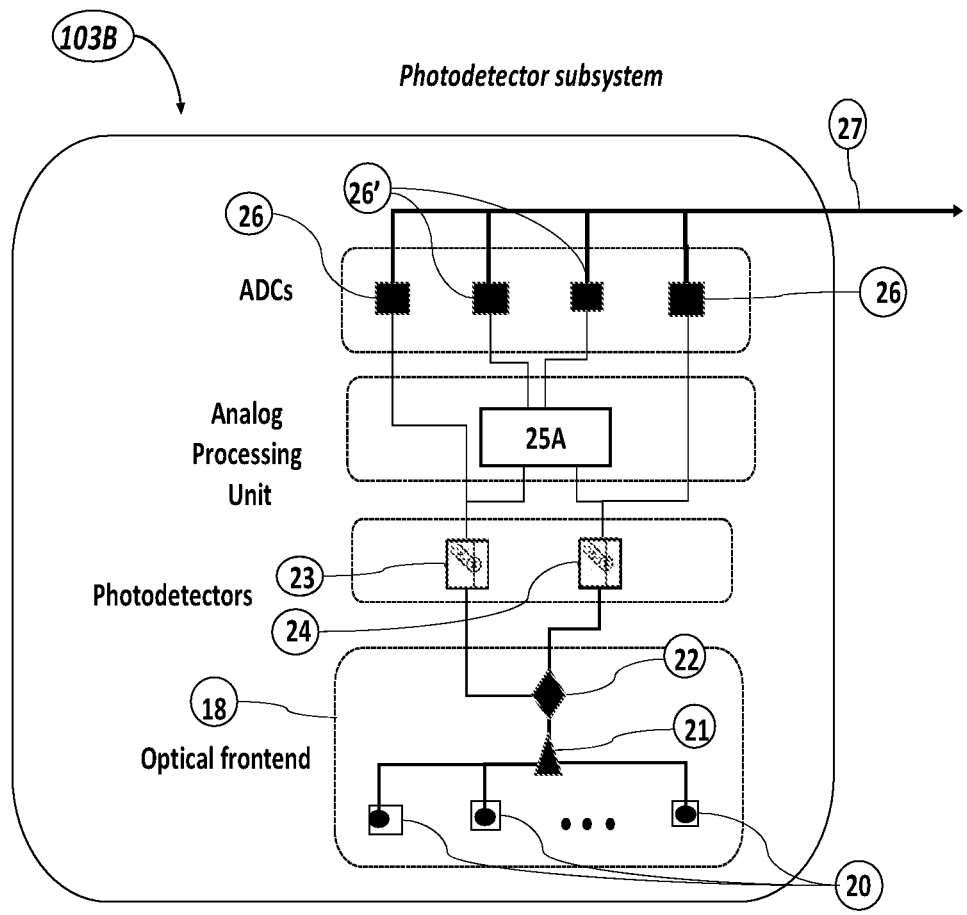
FIG. 10 is a schematic drawing of an embodiment of a photodetector subsystem when a delayed signal is used for SNR and resolution improvement.

Each detection probe 106 in FIG. 3 consists of an illumination subsystem 102B described in detail in conjunction with FIG. 6; a photodetector subsystem 103 (comprising either 103A or 103B described in detail in conjunction with FIG. 9 and FIG. 10, respectively); and a control and data processing subsystem 104.

Each detection probe 106 is an autonomous unit that receives input beams from laser sources subsystem 101 via an optical multiplexor, typically a 1×2 optical multiplexer 4B (FIG. 6), converts the optical beams first to analog electronic signals, and then converts the analog signals to digital signals. These conversions are effected in photodetector subsystems 103A or 103B. The digital signals are then transmitted to control and data processing subsystem 104 where they are processed and the resultant data exported as a full Raman spectrum, via an Ethernet connection from the control and data processing subsystem 104 to server 105. The conversion of the input laser beams first to analog signals and then to digital signals is discussed in greater detail in conjunction with FIGS. 9 and 10.

Reference is now made to FIG. 4 where laser sources subsystem 101 is shown. Subsystem 101 is comprised of a tunable pump laser 1 whose emitted beam impinges on an entrance port of an optical combiner 3; two or more fixed wavelength lasers form an array, herein denoted as a Stokes laser array (SLA) 2. Each of the lasers in the array is optically coupled via fiber optic cables and/or waveguides and/or connectors 7 with optical combiner 3. The beams of lasers 1 and 2, which are pulsed substantially simultaneously that is within fractions of picoseconds to fractions of microseconds of each other, are combined in combiner 3 and brought to illumination subsystem 102A or 102B from optical combiner 3 via fiber optic cables and/or waveguides and/or connectors 60 (described in detail in conjunction with FIG. 5 or FIG. 6, respectively). A timing generator 8 provides all activation/synchronization signals required by pump laser 1 and Stoke laser array 2. These produce all the necessary combinations of wavelength differences required to generate a spectrum having a full pre-defined Raman spectral range.

Figure 5:
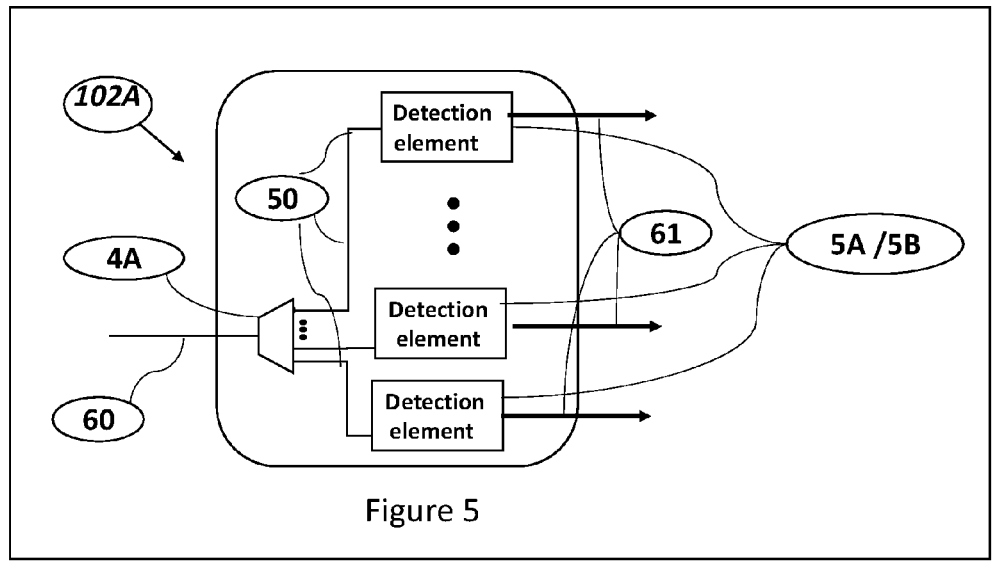
FIG. 5 is a schematic drawing of an embodiment of an illumination subsystem that may be used in the spectrophotometer system of FIG. 2.
Figure 7:
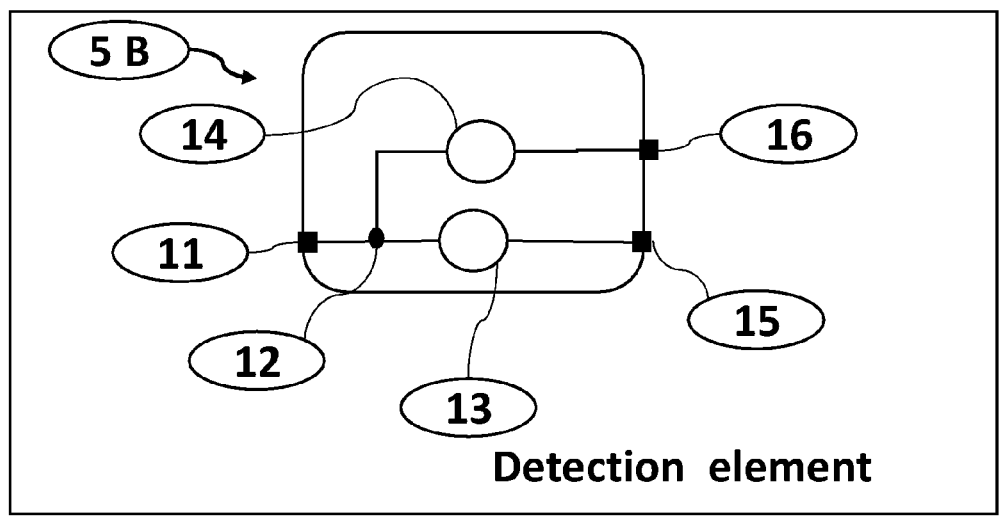
FIG. 7 is a schematic drawing of an embodiment of a detection element (DE) that includes two chambers, one chamber containing a reference sample and the other chamber containing either a target sample or a calibration sample and that may be used in the illumination subsystems shown in FIG. 5 and FIG. 6.
Figure 8:
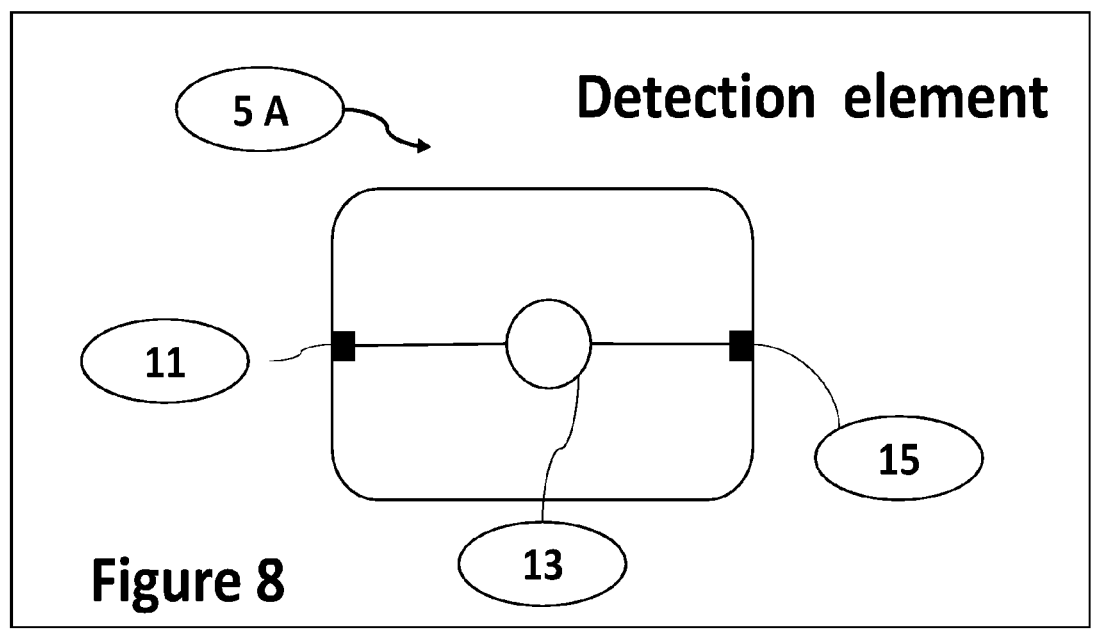
FIG. 8 is a schematic drawing of an embodiment of a detection element (DE) that includes only one chamber and contains a target sample or a calibration sample used in the illumination subsystem shown in FIG. 5 or FIG. 6.

Reference is now made to FIG. 5, where the Illumination subsystem 102A of the centralized configuration 100A of FIG. 2 is schematically shown. Subsystem 102A is comprised of an optical time-division multiplexer (TDM) 4A, or other optical element having similar functionality, optically coupled by fiber optic cables and/or waveguides and/or coupling elements 50 with detection elements 5A or 5B, these latter discussed below in conjunction with FIGS. 7 and 8. The illumination subsystem comprises one or more detection elements that contain a target sample. As shown in FIGS. 7 and 8, the optical beams emerging from detection elements 5A and 5B are brought to photodetector subsystem 103A with fiber optic cables/waveguides and/or coupling elements denoted as element 61.

Reference is now made to FIG. 6 which schematically shows an Illumination subsystem 102B used in the distributed configuration 100B of FIG. 3. This subsystem is comprised of a single detection element 5A/5B (FIGS. 7 and 8). The detection element may contain a target sample or a calibration sample. A multiplexer (MPX) 4B located in or near the laser beam inlet port to each of one or more detection probe(s) 106 in FIG. 3 is in optical communication with the combined Stokes and pump laser beams arriving from laser sources subsystem 101. When a given detection probe 106 is activated by the system server 105, multiplexer 4B of that detection probe 106 guides the combined pump and Stokes laser beams received through fiber optic 60 from combiner 3 into the detection element 5A or 5B via fiber optic 50. When a detection probe 106 is inactive, its multiplexer 4B transfers the laser beam to an adjacent detection probe 106 via fiber optic 60. This process repeats itself until the detector elements in each of the detection probe(s) 106 have been illuminated via operation of their respective multiplexer(s) 4B General reference is now made to FIG. 7, FIG. 8. FIG. 9 and FIG. 10. As described in the background section, for every target molecule, when the condition $\Omega=\Delta\omega$ is met, $\Delta I_p$ and $\Delta I_s$ is proportional to concentration. The emitted optical signals $I_p$ and $I_s$ are converted to analog electronic signals, pump signal $S_p$ and Stoke signal $S_s$, respectively, when both the pump and Stokes lasers are activated. These are characterized by the following equations:

$$S_p = I_p - \Delta I_p + n_p \quad \text{(Eq. 3)}$$

and $$S_s = I_s + \Delta I_s + n_s \quad \text{(Eq. 4)},$$

where $I_p$ and $I_s$ are the Stoke and the pump beam intensities illuminating the sample; $\Delta I_p$ and $\Delta I_s$ are the changes of the illuminating beam intensities previously described resulting from the SRS phenomena; and $n_p$ and $n_s$ are the system noise of the pump laser and Stokes laser, respectively.

At low concentrations of target materials, the nature of the signals is characterized by the following equations:

$$\Delta I_p << I_p \text{ and } \Delta I_s << I_s \text{ (that is low relevant signals);}$$

$$\Delta I_p < n_p \text{ and } \Delta I_s < n_s \text{ (that is low SNR); and}$$

$\Delta I_p = \Delta I_s \propto I_p \times I_s$ (proportional to the product of the laser beam intensities). When only the pump laser is activated, $S_p$ is represented by $$S_p = I_p + n_p. \qquad (Eq.\ 5).$$

Since SRS is used under conditions where SNR is low, it is difficult to extract $\Delta I_p$ and $\Delta I_s$ from the received electronic signals $S_p$ and $S_s$. It is clear to persons skilled in the art, that converting the analog signals $S_p$ and $S_s$ derived from $I_p$ and $I_s$ to digital signals without losing the relevant data $\Delta I_p$ and $\Delta I_s$ requires very accurate analog-to-digital convertors (ADCs), typically (14-18 bit ADCs). With nanosecond laser pulses, these ADCs must be very fast (GHzs). Such ADCs typically are custom-made and very expensive, fit for academic and research institutes but unsuitable for commercial systems as noted above.

Application of analog signal processing to the analog signals $S_p$ and $S_s$, prior to their digital conversion as taught in the present invention, enables extraction of the relevant data $\Delta I_p$ and/or $\Delta I_s$ using simpler ADCs (for example, 8-10 bit ADCs), while obtaining high SNR and high resolution.

This processing can be achieved by employing a variety of analog processing solutions. For the sake of example only, two possible solutions (embodiments) are provided:

1) In a detection element that includes two detection chambers, one for a target sample and the other for a reference sample, both chambers are illuminated substantially simultaneously. A small portion of the combined pump and Stoke laser beam intensities is used to illuminate the reference sample. Since the reference sample is different from the target sample only in the material(s) being identified and/or quantified, comparing signals extracted from the emitted beams of the target sample and the reference sample allows for isolation of the signal resulting from the material or materials being identified and/or quantified.

2) In a detection element that includes one detection chamber, no reference sample is used. The target/calibration sample is compared at two distinct times, separated by a few nano-seconds (e.g., 4 ns.). When one signal is the pump laser signal only and the other signal is a combined pump laser plus Stokes laser signal, subtraction of one signal from the other provides just the SRS signal.

The two above solutions for improving the SNR and resolution will now be discussed in greater detail.

Reference is now made to FIG. 9 in conjunction with FIG. 7. In this solution, a small portion of the combined pump and Stokes laser beams illuminates a chamber containing a reference sample. The emitted beam from this chamber is a representation of the beam without the SRS signal ($S_p = I_p + n_p$). Feeding this signal to the analog processing unit (APU 25 in FIG. 9) together with the emitted beam from the chamber containing the target/calibration sample which includes the SRS signal ($S_p = I_p - \Delta I_p + n_p$) allows for the extraction of the SRS signal ($\Delta I_p$) in high resolution and high SNR FIG. 7 is a schematic diagram of a detection element that includes two chambers, one containing a reference sample and the other containing a target sample or a calibration sample. The combined pump and Stokes laser beam arrives at laser beam inlet 11 via fiber optics 50 from laser source subsystem 101 and then proceeds to an optical beam splitter 12 where the intensity of the combined beam is split. Beam splitter 12 may herein also be denoted as an intensity beam splitter. As a typical, but non-limiting ratio, the beam may be split in a 10/90 ratio. The beam with 10 percent of the total impinging intensity then proceeds to a detection element with a chamber containing the reference sample 14. The beam with 90% of the total impinging intensity is passed through a detection chamber containing a target sample or a calibration sample 13. The beams passing through reference chamber 14 and target/calibration chamber 13 are delivered to laser beam outlets 16 and 15, respectively, which are optically connected to a photodetector subsystem 103A discussed below in conjunction with FIG. 9.

FIG. 9 to which reference is now made, shows a schematic diagram of an embodiment of the photodetector subsystem 103A where a reference sample is used for SNR and resolution improvement. The emitted laser beams from detection chambers 13 (FIG. 7) containing the target sample(s) or calibration sample(s) of various detection elements 5B (FIG. 7) are brought to inlets 19. The emitted laser beams from detection chambers 14 (FIG. 7) containing reference sample(s) in various detection elements 5B (FIG. 7) are directed to inlets 20, The beams from the target sample(s) or the calibration sample(s) are brought to one beam combiner 21 while the beams from the reference sample(s) are brought to a second beam combiner 21.

The combined beam is brought from each beam combiner 21 to a separate wavelength beam splitter 22. These splitters are typically dichroic optical filters, but they are not necessarily limited to such filters. Any other optical elements capable of performing the same function may also be used. These filters separate the combined pump laser and Stokes laser beams arriving from illumination subsystem 102A (FIG. 2) or 102B (FIG. 3). Each of the two pump laser beams (reference and target) is delivered to a different one of two photodetectors 23 shown. Each of the two Stokes laser beams is brought to a different one of two Stokes beam photodetectors shown as 24. It should be noted that instead of a single photodetector as shown in FIG. 9, in other embodiments there may be a greater plurality of photodetectors 23 and 24 each dedicated to a different individual pump or Stokes laser beam arriving from the reference samples, target samples and calibration samples of illumination subsystem 102A (FIG. 2). Photodiodes serve as photodetectors 23 and 24 but this is not to be deemed limiting. Other types of photodetectors such as photomultipliers may also be used.

The resulting analog electronic signals generated by photodetectors 23, 24 are then brought to an analog processing unit (APU) 25 which carries out analog signal manipulation and processing. The APU allows for improvement in resolution and signal-to-noise ratio (SNR). The analog signals manipulated by APU 25 are then brought to the analog-to-digital converters (ADCs) 26' where the signals are digitized.

Analog signals are also brought directly from photodetectors 23, 24 to their respective ADCs 26 where the signals are digitized.

Note that in photodetector subsystem 103A, ADCs 26 convert analog voltage (and/or current) signals received directly from photodetectors 23 and 24 to digitized signals while ADC 26' converts analog signals to digitized signals only after the analog signal has been further manipulated by APU 25.

ADCs 26, 26' and analog manipulation processor (APU) 25 are in electronic communication with data bus ADC data collection and control lines 27. Bus 27 leads to an electronic interface with a control and data processing subsystem 104 (FIG. 2, and FIG. 3).

Reference is now made to FIG. 10 in conjunction with FIG. 8. In this embodiment of the present invention, only one detection chamber is used in each detection element (FIG. 8). The fact that the pulse duration of the pump laser beam is longer than the pulse duration of the Stoke laser beam is utilized to extract the SRS signal ($\Delta I_p$) from the emitted pump signal ($I_p$). Thus, during portions of the time, when the Stokes beam and the pump beam are together illuminated on the target sample/calibration sample, the emitted pump signal ($S_p$) contains the SRS signal ($\Delta I_p$). When the pump beam alone is illuminated, that is without a delayed Stokes beam, on the target sample/calibration sample, the emitted pump signal ($S_p$) does not contain the SRS signal as in Eq. 5. Conveying both signals into the analog processing unit (APU) together using a delay line enables the extraction of the SRS signal ($\Delta I_p$) in high resolution and better SNR.

FIG. 8 is a schematic diagram of a detection element that includes one detection chamber only. The combined pump and Stokes laser beam arrives at laser beam inlet 11 from laser sources subsystem 101 (FIG. 4). The beam passes through detection chamber 13 which contains the target or calibration sample to be analyzed and is delivered to laser beam outlet 15 in optical communication with photodetector subsystem 103B (FIG. 10) discussed below.

FIG. 10 shows a schematic diagram of the photodetector subsystem 103B in which a delayed signal is used for SNR and resolution improvement. This photodetector subsystem is similar to photodetector subsystem 103A, described above (FIG. 9), with the main difference being that only one set of optical frontend elements (inlet 19, combiner 21 and splitter 22) is used. Only one set of photodetectors 23, 24 is used to convert the pump laser and Stokes laser to analog signals. One photodetector converts the pump laser beam to an analog electronic signal while the second photodetector does the same to the Stokes laser beam. These signals are brought to a dedicated analog processing unit (APU) 25A which carries out different and specific analog signal manipulations, examples of which are discussed below, using the target/calibration signal only, detailed below. The output of the APU 25A and the original analog signals generated by photodiodes 23, 24, are converted to digital signals by a set of analog-to-digital converters (ADCs) 26' and 26 employed as discussed in conjunction with subsystem 103A. Similarly, the digitized samples are sent to the control and data processing subsystem 104 as with subsystem 103A.

Some of systems/components/elements of this invention discussed above will now be discussed in greater detail.

A. The Laser Sources Subsystem 101 (FIG. 4)

The laser sources subsystem functions to generate a pair of laser pulses that is defined as to timing, power, wavelength, bandwidth etc. Such definitions are updated regularly by the adaptive calibration algorithm mentioned above and discussed further below. The laser sources subsystem comprises:

i. A Pulsed Tunable Pump Laser 1—

A tunable laser is a laser whose wavelength of operation can be altered in a controlled manner. Lasers are a combination of a gain media and an optical cavity and these define the laser's wavelength. An optical cavity or optical resonator is an arrangement of mirrors that forms a standing wave cavity resonator for light waves. For some types of lasers the laser's cavity length can be modified, and thus they can be continuously tuned over a specific wavelength range. External cavity lasers using a MEMS structure for tuning the laser cavity length can be continuously tuned over a specific wavelength range. The present invention is unique in that a wide spectral range is achieved by using a narrow range tunable laser. The advantages of a narrow range tunable laser are simplicity, reliability, small size and cost. This type of laser has a typical, but without intending to limit the invention, 5-40 nm tunable range laser with laser pulse durations of from about 0.001 to about 100 nanoseconds. The laser's tunable scanning speed is of the order of 40 nm per one second (1 sec) or faster. Any of many tunable lasers may be used as the pump laser. The general features of a tunable pump laser (TPL) which can be used may be summarized as: fast tunable; highly stable; center wavelength in between 650 nm-800 nm; tuning range, typically at least 20 nm; and laser pulse power of at least 100 mW. "Fast tunable" indicates that the full tuning range is scanned in less than 0.1 s. "Stable" indicates that there is no mode and frequency hopping and that the variation in the laser's intensity is limited to a known range. All values cited in this paragraph are exemplary only and non-limiting. In another embodiment of the present invention, the pump signal is amplified using a taper amplifier that operates in the same wavelength range as the tunable laser thus providing a stronger signal through the TPL's whole range.

ii. An Array of Stokes Pulsed Lasers (SLA) 2—

The number of Stokes lasers in the array is directly related to the range of the tunable laser. The lasers in the array should typically provide a wavelength difference between two successive Stokes laser frequencies of less than or equal to the tuning range of the tunable pump laser. In practice, the array may comprise of 2-10 lasers but it should readily be appreciated that more than 10 lasers may also be used.

Only one laser in the array is activated and pulsed at a given time and it is combined with the pulsed beam of the tunable laser to form a single beam. The combined pulse and Stokes laser beam impinges on the material to be analyzed or the calibration material and the reference material. The pulse of the Stokes lasers may typically be in the 0.05-90 nanosecond range and each Stokes laser in the Stokes laser array will provide a pulse at a different fixed wavelength. The laser array, for example could be formed of a set of single mode, single emitter, high peak power pulsed diode lasers or fiber lasers or other suitable laser types. All values cited in this paragraph are exemplary only and non-limiting.

In order to attain adequate detection capability at very low concentrations, the Stokes laser pulse should be of very high intensity. A very short pulse duration and a low duty-cycle, typically 0.01%-1% of the cycle, keeps the system in an average low power state, preventing heating, lowering power consumption, and reducing cost. However, the use of lasers in the laser array having longer pulse times is also possible.

The Stokes laser array contemplated typically comprises lasers that lack at least one of the following: temperature stabilization, wavelength stabilization, and amplitude stabilization. The system described herein below compensates for instabilities of these array characteristics through the use of an adaptive calibration algorithm.

The SLA generates Stokes laser pulses with the required characteristics (wavelength, band-width, timing and intensity) and, as noted above, it is combined with the pump laser pulse. Combination of each of the lasers in the array with one of the allowable settings of the tunable pump laser generates laser beams that cover the pre-defined range of required wavelength differences used to generate the Raman spectrum of a target material or materials.

If the lasers of the array do not generate enough intensity an alternate approach may be used. Each laser of the SLA may comprise a laser driver (electronic component) which drives a seed laser. The beam of the seed laser would then be amplified by an optical amplifier, typically, but without intending to limit the invention, a tapered (TP) optical amplifier. The amplified beam would then be combined with an amplified tunable pump laser beam using an optical combiner as discussed above.

Generating the laser pulse with the laser driver as discussed immediately above is but one way of generating the array of laser beams required. One skilled in the art would readily realize, that an optical modulator may be used on the output beam of a continuous wave (cw) laser as an alternative to a pulsed laser driver.

Since the pump and Stokes laser beams require proper coupling, collimating optics and/or other optical components may be included and positioned in any of several places in the laser sources subsystem 101 and/or the illumination subsystem 102A and 102B discussed above. These components and their optimal positioning are readily known to persons skilled in the art.

Table I below is a summary of the acceptable and preferable parameter ranges that are usable with the spectrophotometer system of the present invention discussed herein.

Typical, but non-limiting, inexpensive lasers that can be used in the laser sources subsystem of the present invention are diode lasers purchasable form QPhotonics (Ann Arbor, Mich.). Their catalogue number is QLD −850-150S which represents a free space, single mode diode laser, 170 mW, with spectral width of 0.5 nm and wavelength for example 850 nm.

iii. An Optical Combiner 3—

This element receives via fiber optic cables and connectors, and combines the beams of the pump laser and the activated Stokes laser. Since the Stokes lasers are activated one at a time in a predetermined sequence, the combined single output beam varies in frequency as the Stokes laser being activated is varied and the pump laser frequency is varied. Without limiting the invention, the combiner for example, may be an optical diffraction grating combiner, a polarized, dichroic filter or a fiber beam combiner.

iv. A Timing Generator 8—

This may be, but without intending to limit the invention, a programmable digital logic device, for example, a field programmable gate array (FPGA) that generates all the timing signals needed to run the system. It provides:

Activation and operation signals to the tunable laser e.g. laser on/off, scanning rate, tuning range.

Synchronizes the activation of the lasers in the SLA by activating "ON trigger" to one of the lasers in the array.

The timing generator in some of the embodiments of this invention may optionally synchronize the following elements:

Synchronizes the optical time domain multiplexer (TDM) 4A in illumination subsystem 102A operation to enable sequential illumination of the various target detection elements and the at least one calibration detection element.

Provides synchronization signals to the photodetectors 23, 24 and the ADCs 26, 26' in the photodetector subsystem.

Provides laser activation synchronization signals to the DSP/CPU 9 to enable the DSP/CPU to associate each result read from the ADCs with the specific combination of the pump and Stokes lasers that generated those results. It also enables the DSP/CPU to save and reorder the interleaved signals in the correct order.

However, in other embodiments these elements may be synchronized by other clock sources.

The timing generator is controlled and pre-programmed by the server 105 (FIGS. 2, 3) and upon activation it runs the required spectrum generation sequence autonomously.

TABLE 1

Laser and detection parameters

| Parameter | Units | Acceptable range | Preferable range |
|---|---|---|---|
| Pump laser pulse duration | Nanosecond | 0.001-1,000 | 0.01-10 |
| Stokes laser pulse duration | Nanosecond | 0.0005-900 | 0.005-9 |
| Laser spectral range wavelength (Stokes and pump lasers together) | Nanometer | 600-1500 | 700-1,100 |
| Pump laser tuning range | Nanometer | 5-100 | 20-40 |
| Multiplexer rate | Hz | 0.01-100,000 | 10-10,000 |
| Number of repetitive illuminations with given parameter settings for increasing SNR | Number | 2-10,000 | 64-1,024 |
| Raman emission spectral range | Wavenumber ($cm^{-1}$) | 6,500 | 3,000 |
| Spectrum resolution | Nanometer | 0.01-3 | 0.1-2 |
| Stokes laser duty-cycles | Percentage | 0.0001%-20% | 0.001%-1% |

Synchronization of the Stokes laser array (SLA) 2 and the pump laser (2, 1, FIG. 4) produces all necessary combinations of wavelength differences required to generate to a full pre-defined Raman spectral range. Typically, but without intending to limit the invention, the resolution of the spectral range is between 0.1 nm to 2 nm; the lasers of the laser array are activated at typical repetition rates of 64-1024 repetitions per spectrum point; and have a typical duty-cycle of 0.001%-1%.

In the embodiments herein discussed, the SRS spectrophotometer system being taught employs a tunable pump laser and a fixed wavelength Stokes laser array. However, the invention contemplates embodiments which comprise a single tunable Stokes laser and a fixed wavelength pump laser array. For these embodiments only a minimum number of modifications to the system described would be required. These modifications can readily be effected by persons skilled in the art.

B. The Illumination Subsystem (102A, 102B)

i. A time division optical switch 4A (FIG. 5)

is a single "one-to-many" optical switch, having one input and as many outputs as the number of detection elements in the centralized configuration (FIG. 2). In the distributed configuration (FIG. 3), many "one-to-two" optical switches 4B (FIG. 6) are used. The switch sends the combined pump laser beam and Stokes laser beam provided by laser sources subsystem 101 to a different detection element 5A or 5B every few milliseconds. Without intending to limit the invention, the switch 4A or 4B may for example be an opto-mechanical switch based on micro electro-mechanical system (MEMS) micro mirror technology. It may also be an optical time domain multiplexer (TDM) that transfers the beam to a different target every few milliseconds.

ii. Detection chamber 13 or 14 (see discussion above in conjunction with FIGS. 7 and 81:

The detection chambers may, for example, be a Pyrex cuvette with few or no Raman spectral peaks and/or fluorescence in the wavelength range being analyzed and thus produce minimal obscuration of experimental spectral data.

The detection chamber may be a single pass chamber where the illumination beam passes through the target/calibration/reference sample only once. Alternatively, it may be a multipass chamber where the illumination beam passes through the target/calibration/reference sample many times. It may contain two or more focusing mirrors to redirect the beam back to the sample several times until it is reflected out of the chamber. In spectroscopy, such an apparatus is known as a Multipath Spectroscopic Absorption Cell and can be implemented with one of many multipass cell configurations, for example, with a White cell or a Herriott cell.

iii. An optical intensity beam splitter 12 (FIG. 7)

When a reference sample is used for noise reduction and resolution improvement each detection element includes an optical intensity beam splitter. This splitter is positioned before the detection chambers 13 and 14, and splits the combined pump and Stokes laser beam received from optical switch or multiplexer 4A/4B so that, for example, 90% of the intensity of the combined beam illuminates the target sample or calibration sample while 10% illuminates the reference sample in a given detection element. The 90/10 split ratio is exemplary only and other ratios may also be used. The beam splitter may be a reflecting neutral density filter, but other optical elements known to persons skilled in the art having similar functionality may also be used.

C. The Photodetector Subsystem (FIG. 9 and FIG. 10)

i. The optical frontend 18 (FIG. 9 and FIG. 10)—

The optical frontend contains optical elements to handle the received beams prior to their conversion to electronic signals.

a. Target and/or calibration optical inlet port 19

This port(s) receives optical beams arriving from the illumination subsystem via optical fiber cables after the beams have passed through detection chambers 13 containing target or calibration samples via an optical fiber. This port is a standard optical fiber interface. In the centralized configuration (FIG. 2) the beam from each detection chamber arrives via a dedicated inlet port. In the distributed configuration (FIG. 3), the optical frontend may be coupled to the detection element so as to provide a free-space optical interface. In such an embodiment, inlet port 19 is not required. In other embodiments, the optical frontend may be separated from the detection element and connected via optical fiber.

b. Reference optical inlet port 20—

This is identical to the target and/or calibration optical inlet port 19 described above, and is used to connect the detection chamber 14 containing the reference sample to the relevant optical front-end.

c. Beam combiner 21—

In the centralized configuration, the beams for each detection element arriving via inlet port 19 are combined to a single beam. This can be done using optical wave guides or using optical TDM (time division optical multiplexer) synchronized to the illumination beam optical TDM 4A. When a reference sample is used, an additional beam combiner is used to combine the beams arriving from the reference chambers. In the distributed configuration, beam combiner 21 is not required.

ii. Photoelectric conversion elements (PCE) 23, 24.—

Also named photodetectors, without attempting to distinguish the terms. These elements convert each laser beam to an analog electronic signal (current/voltage). Typically, one PCE converts the pump laser beam to an analog electronic signal while a second PCE converts the Stokes laser beam to an analog electronic signal. The photoelectric conversion elements often denoted herein as photodetector elements 23, 24 are typically photodiodes but they also may be photomultipliers or any other type of opto-electrical conversion element. Each photodiode, for example a PIN photodiode, converts one of the received laser beams into analog electronic signals, providing an electronic signal current/voltage proportional to the intensity of the laser beam.

iii. An analog processing unit (APU) 25 and 25A

The electronic analog signal (current/voltage) obtained from the photoelectric conversion elements 23 and 24 are used as input for APU 25 or 25A. This processing unit manipulates the analog signal so that the signal to noise ratio (SNR) and the resolution of the signal improves. This manipulation is intended to remove non-SRS data, thereby reducing background and laser noise. It is also intended to eliminate any residual Stokes signals that leak through non-ideal dichroic filter 22 into the pump beam photodetector.

a. An example of an analog manipulation which may be implemented by analog processing unit (APU) 25 when a reference sample is used as in FIG. 7 and FIG. 9 (subsystem 103A) may be based on the following function:

$$F1 = \alpha \times I_{p\ reference} - I_{p\ target} - \beta \times I_{s\ target} \quad [Eq.\ 6]$$

In this function, $\alpha$ is the target sample to reference sample beam intensity split ratio (see Illumination subsystem (FIG. 7) above) while $\beta$ represents the residual intensity of the Stokes beam in the pump beam due to the non-ideal performance of, for example, the dichroic filter 22 which serves as the beam splitter. Reducing the $I_{s\ target}$ signal eliminates the Stokes beam noise in the pump signal. The manipulation $\alpha \times I_{p\ reference}$ removes the beam intensity background noise that contains no SRS information.

b. An example of an analog manipulation which may be implemented by analog processing unit (APU) 25 when a delayed signal is used as the reference in FIG. 8 and FIG. 10 (subsystem 103B) may be based on the following function:

$$F2 = \gamma(I_{p(t-T)} - I_{p(t)}) - \mu \times I_s \quad [Eq.\ 7]$$

Figure 11:
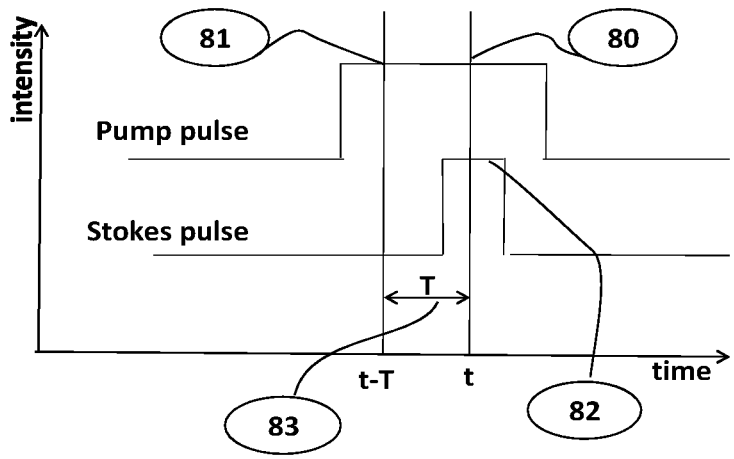
FIG. 11 is a timing diagram of the pump and the Stokes laser pulses providing a delay signal as discussed in conjunction with the photodetector subsystem of FIG. 10.

Reference now is made to FIG. 11 where a timing diagram of the pump and the Stokes signals is shown. In the function in Eq. 7, pump signal $I_p$ at time t 80 when the Stokes pulse 82 is present is subtracted from the pump signal $I_p$ at time (t−T) 81, when the Stokes pulse 82 is not present. T 83 is a constant time that represents the delay between a pump laser pulse that is illuminated together with a Stokes laser pulse and a pump laser pulse that is illuminated without a Stokes laser pulse. The result is multiplied by a predefined gain $\gamma$, while $\mu$ represents the residual intensity of the Stokes beam in the pump beam. This function removes the original beam intensity and background noise and amplifies the SRS information. The required delay can be implemented by using a longer connecting line that generates a delay of T sec on the electronics signal; each 30 cm of signal path length generates an approximate 1 ns delay. Other methods for providing the delay should be readily evident to persons skilled in the art.

It should be noted that the functions in Eq. 6 or Eq. 7 above, represents only two of many possible manipulation functions that may be employed by analog processing units (exemplified in APU 25 and APU 25A).

While in the embodiments shown in FIGS. 9 and 10, the APU operates on real time analog signals, in other embodiments, a manipulation processor may manipulate non-real time digital data.

iv. Analog-to-digital converters (ADCs) 26, 26':

The analog outputs of all of the photodetectors and the analog processing units are converted into digital information using analog-to-digital converters (ADCs). ADCs 26 convert the voltage/current of the analog signals when no analog manipulation has been performed on them; ADCs 26' convert analog signals after the signals have undergone an additional analog manipulation. The digital information provided by ADCs 26, 26' is then conveyed to DSP/CPU 9 discussed below.

In other embodiments, all the analog data passes through APU 25 and is converted by ADC 26 to digital signals and brought to the DSP/CPU 9 discussed below.

Alternatively, or additionally, in yet other embodiments of this invention, noise reduction functionality similar to that described above may be done in non-real-time, digitally in DSP/CPU 9 without use of an analog manipulation processor. The digital signals are sent from ADCs 26 to control and data processing subsystem 104 and stored in these processing units' memory, at the completion of systems' 100A and 100B illumination sequence and prior to further data processing, the latter discussed below in greater detail.

Typical, but non-limiting, inexpensive ADCs that can be used in the photodetector subsystem of the present invention are ADCs purchasable from Texas Instruments (Dallas, Tex.). Their catalogue part numbers are ADC08500 (8 bits, 500M samples per second) and ADC10DV200 (10 bit 200M samples/second) and both are serviceable.

D. Control and Data Processing Subsystem 104

The control and data processing subsystem 104 comprises a digital signal processor (DSP) and/or central processing unit (CPU) 9. Subsystem 104 generates control system parameters. It also performs additional digital processing on the digital output signals received from photodetector subsystem 103A or 103B further enhancing SNR, reducing noise, and correcting the collected data by employing adaptive calibration (discussed below). In some embodiments, a DSP can be substituted by a CPU; in other embodiments, the DSP and CPU are both present; and in yet other embodiments, the CPU may be an off-line external CPU.

There are data and control lines 27 providing for electronic communication between analog manipulation processors (APU) 25 and DSP/CPU 9. Similarly, ADCs 26 and 26' are in electronic communication with, and all of their digital output is sent to, DSP/CPU 9 via lines 27.

In some embodiments of the present invention, there may be a need for additional programmable logic in the control and data processing subsystem to temporarily store the digital output received from the ADCs prior to further processing.

The DSP/CPU 9 runs one of many well-known general digital signal processing algorithms to further improve SNR, for example an algorithm averaging the multiple readings of a given sample and/or by using a non-real time lock-in-amplifier. It also runs a non-real time adaptive calibration algorithm which inter alia also assists in calibrating the hardware (HW), for example by compensating for wavelength drift, temperature and beam intensity variations, and other instabilities.

The DSP/CPU 9 may be, but without the intention of limiting the invention, for example, a general purpose embedded CPU or a dedicated DSP chip.

The system's SRS software (SW) is run on the DSP/CPU 9 and it inter alia includes three SW packages: a SRS spectra data base; a digital signal processing (DSP) algorithm; and SRS control SW.

The database SW is used by DSP/CPU 9 to save the measured SRS spectral data in the order required for use by the digital signal processing algorithm.

E. System Server 105—

The server contains all central control elements and the interface to host system or users. It also controls the system parameters discussed herein, for example, laser input current-voltage, laser temperature correction, analog manipulation processor parameters and timing generator parameters.

The subsystems described above have been discussed in one configuration and embodiment. These are to be viewed as exemplary only. Other configurations and embodiments may also be used and are readily derivable by persons skilled in the art with the assistance of the configuration given. These other configurations and embodiments are contemplated as part of the present invention.

Method of Spectral Scanning and Data Collection Using the SRS Spectrophotometer System of the Invention The method of spectral scanning and data collection using the SRS spectrophotometer system of the present invention requires running several different loops over each of the lasers in the laser array in order to cover the entire range required for the desired Raman spectrum for each target and calibration sample. A typical implementation of the loops inter alia utilizes a hardware (HW) based timing generator.

Figure 13A:
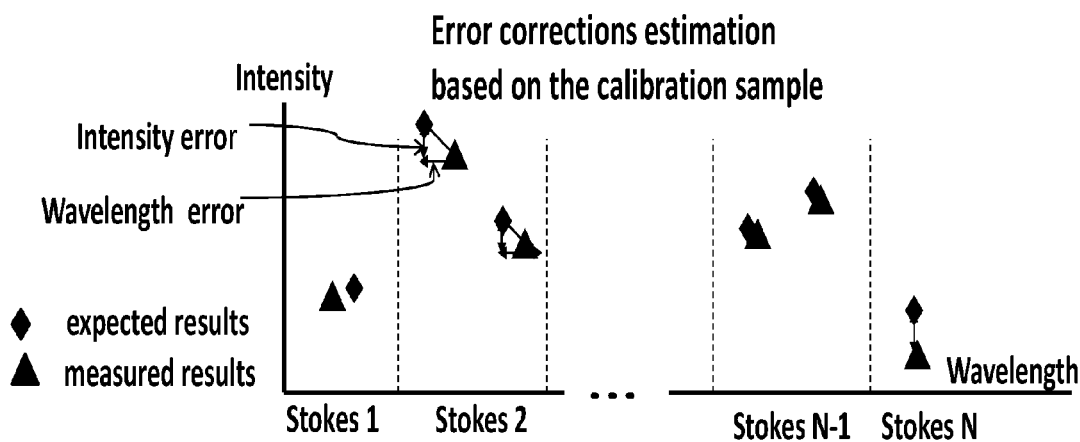
FIGS. 13A and 13B schematically depict an adaptive calibration method usable with the systems of the present invention.
Figure 13B:
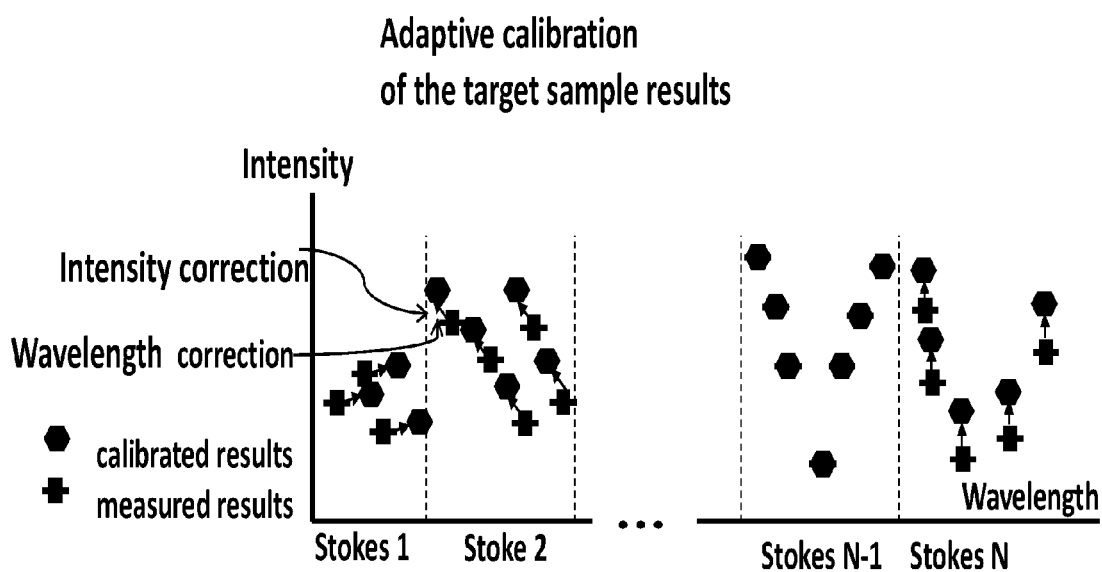
Figure 14:
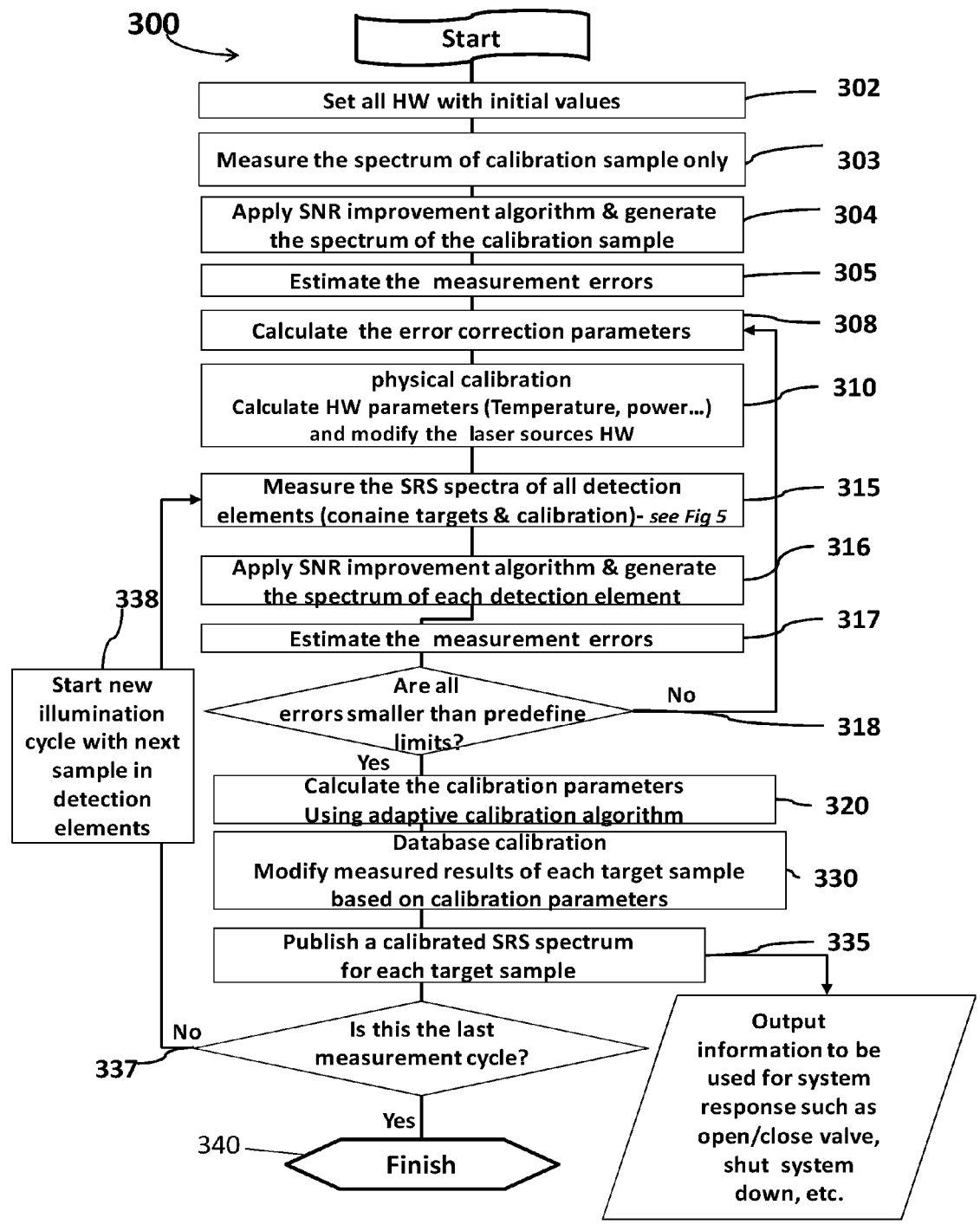

The data collected during each measurement are transferred to DSP/CPU 9. All the collected data is saved in the DSP/CPU 9 memory; at the end of measurement and data processing, SNR improvement is obtained. Calibration algorithms, discussed in conjunction with FIGS. 13A, 13B and 14, are run on the acquired data in order to generate the final spectral fingerprint of the target material(s).

Figure 12:
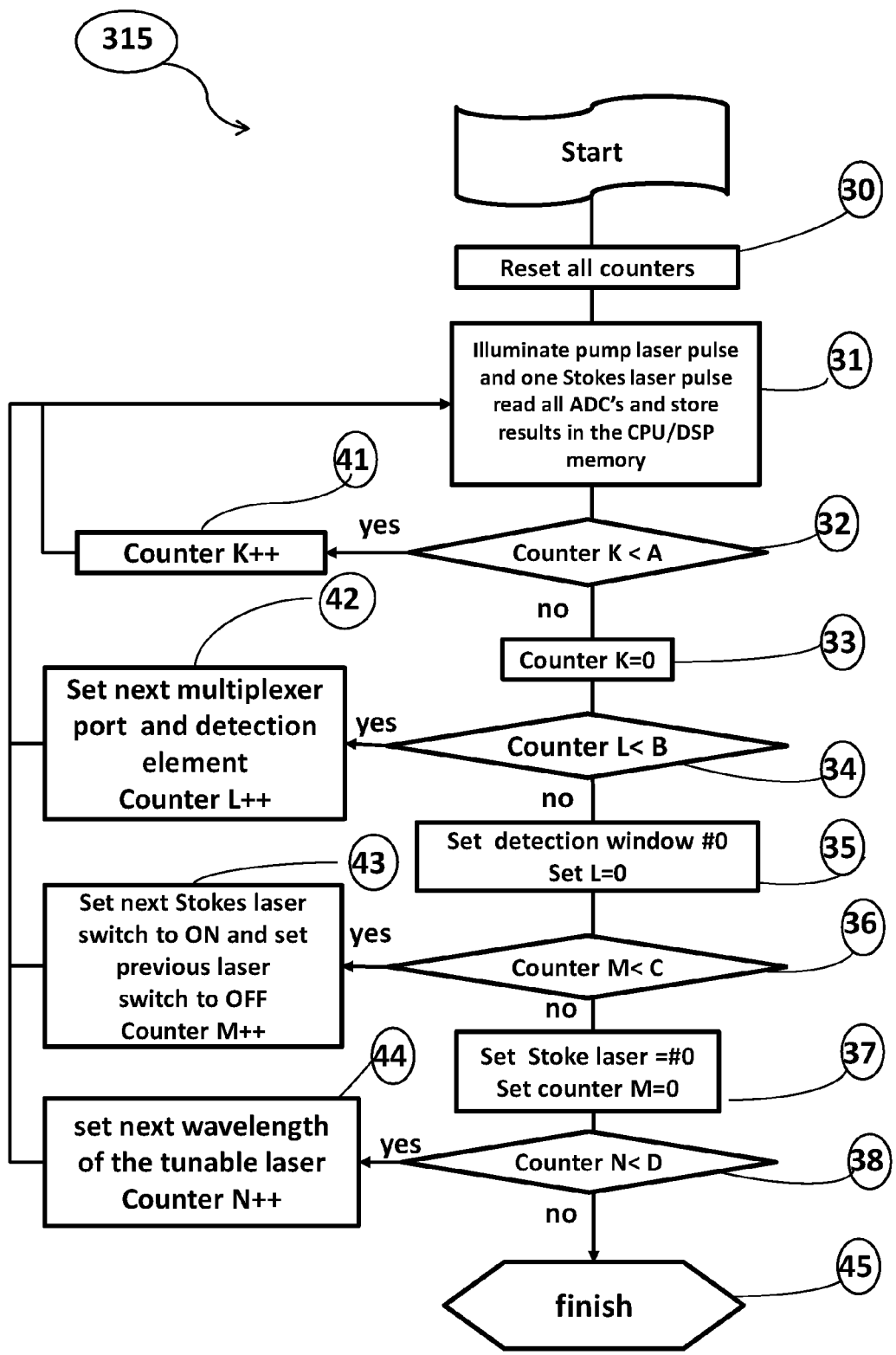
FIG. 12 is a flowchart of an illumination sequence which may be used for spectral scanning and data collection with the spectrophotometer systems of the present invention.

FIG. 12, to which reference is now made, shows a flowchart 315 describing the method of scanning and collecting data using the SRS spectrophotometer system of the present invention. At each illumination point, a pump laser beam and a Stokes laser beam are combined. The combined beam illuminates a target sample or calibration sample and their associated reference samples, in embodiments where reference samples are used. (See discussion of detection element 5B in FIG. 7.)

The sequence includes four different loops:

1. Measurements are repeated several hundred (or thousands of) times using a given set of parameters. The parameters here refer to laser parameters such as laser temperature, input current and analog processing parameters. This repetitive scanning enhances the SNR. (Loop 41, FIG. 12)

2. Looping over detection elements. (Loop 42, FIG. 12)

3. Looping over all fixed wavelength Stokes laser sources in the Stokes laser array. (Loop 43, FIG. 12)

4. Looping over all tunable laser steps. The tunable laser range is scanned in D predetermined steps. Each step requires tuning the tunable pump laser to a specific wavelength from a predetermined series of tunable wavelengths. (Loop 44, FIG. 12)

The combination of the four above loops represents all the laser illuminations needed to cover the entire required spectral range of the target, calibration and, in embodiments when used, reference samples.

In FIG. 12:

A is the number of repetitive illuminations using a specific set of parameter values. Typically, but without intending to limit the invention, A may be $64 < A < 1024$.

B is the number of detection elements containing target, calibration and, in embodiments when used, reference samples. Typically, but without limiting the invention, the number of detection elements can range from 1 to 8;

C is the number of Stokes laser sources typically, but without intending to limit the invention, 2 through 40; and D is the number of tunable points of the tunable pump laser. It is a function of the tunable laser range and of the required spectral resolution, the latter typically, but without limiting the invention, 1 nm.

The steps of FIG. 12 are as follows:

Step 30—Setting hardware (HW) parameters such as laser wavelength, power, temperature, etc. to their setup or default values and setting all counters to their initialization values;

Step 31—Generating short (few picoseconds to a few nanoseconds) substantially simultaneous laser pulses from the pump laser and one of the Stokes lasers for illuminating one of the target or the calibration samples. Read all ADC's and store results in a DSP/CPU 9 memory Step 32—Comparing counter K to determine if its value is less than A;

Step 41—If K<A, increasing counter K by 1;

Step 33—Repeating steps 31, 32 and 41 until K=A in step 32, then set counter K=0;

Step 34—Comparing counter L to determine if its value is less than B;

Step 42—If counter L<B, increasing counter L by 1 thereby setting the next multiplexer port resulting in moving the combined laser beam to the next detection element (target or calibration);

When a distributed configuration of the system is used, the number of detection elements in step 34 is equal to 1 and therefore loop 34-42 is essentially inactive.

Step 35—Repeating steps 31, 32, 41, 33, 34 and 42 until L=B in step 34, then setting detection element # to 0 and L=0;

Step 36—Comparing counter M to determine if M<C;

Step 43—If counter M<C, increasing counter M by 1 and moving to the next Stokes laser by activating its "On" switch while deactivating the previous Stokes laser;

Step 37—Repeating steps 31, 32, 41, 33, 34, 42, 35, 36, and step 43 until M=C in step 36, and then setting Stokes laser # to 0 and counter M to 0;

Step 38—Comparing counter N to determine if N<D;

Step 44—If counter N<D, increasing counter N by 1 and moving to next tunable point (wavelength) of the tunable laser;

Step 45—If N=D in step 38, end looping.

It should be noted that when the tunable laser wavelength of the pump laser is changed as it is in Step 44, a physical change occurs. To vary the tunable wavelength there is a change in the laser optical cavity resonance properties, creating different resonating conditions and producing a wavelength different from the wavelengths of the previous loops. This effects a change in the emission of the pump laser beam.

Similarly, in step 43 when the Stokes laser is changed there is the physical effect of deactivating Stokes laser M and activating Stokes laser M+1.

It should be noted that the looping in FIG. 12 and its description is but one example of an illumination sequence for use with the scanning mode. Other sequences of the loops are also possible.

When using the specific spectral peak mode, data collection would require jumping to specific counter values based on lookup table(s) instead of increasing the counters successively as in FIG. 12. This is but one non-limiting example of a method for employing the specific spectral peak mode.

Method of Using Adaptive Calibration with the SRS Spectrophotometer System of the Present Invention Adaptive calibration is a method in which parameters are changed during the measurement process in order to minimize errors. An exemplary, but non-limiting, method that may be used is the well-known least mean squares filter method. In the present invention, measurement errors may be estimated by measuring the difference between the expected results of the calibration sample(s) to the actual measured results of the calibration sample(s). The differences are measured in the two dimensional space of: 1) wavelength (or equivalently—frequency) and 2) intensity.

Calibration parameters are the calculated correction values needed to modify target sample measurements to compensate for variations in laser source performance. The method for calculation of calibration parameters is adaptive since both current and previous measurements are used to modify the latest measurement results in an accumulated manner. The actual present results are added to prior results when using an adaptive algorithm. Such an algorithm, and only as an exemplary non-limiting example, may be a moving average algorithm. The outputs of the calibration algorithm are calibration parameters in two dimensions, wavelength and intensity, as mentioned above.

In the present invention, separate calibration parameters are calculated for each laser in the Stokes laser array and for the tunable pump laser. The calibration sample composition should provide at least one Raman peak associated with at least one of the laser wavelengths in each of the lasers in the array and a pre-determined wavelength of the tunable pump laser.

The calibration parameters are utilized in the invention in two manners:

1. Physical calibration—This is accomplished by modification of the physical settings of the lasers. Changes in physical settings are calculated based on the above mentioned calibration parameters and known physical characteristics of the laser, as determined by use of a formula or look-up table. This includes, for example, changing the laser diode's temperature in order to change its wavelength and changing the laser amplifier input current in order to change the laser output power. It is possible to distinguish between errors caused by the pump laser from errors caused by the Stokes lasers since the errors caused by the pump laser are common to all results, while the errors caused by the Stokes lasers would be specific to each Stokes laser.

2. Database calibration—Each of the measured results of the target samples is modified according to the calibration parameters in both dimensions, wavelength and intensity. A different set of calibration parameters is used for each Stokes laser. The modified measured results are then used to generate the SRS spectrum of the target samples which is used for identification and/or quantitative analysis of the target samples.

FIGS. 13A and 13B schematically exemplify one possible adaptive calibration method that can be used. FIG. 13A illustrates the error estimation process. The measured results of the calibration sample are compared to expected results for the calibration material at known quantities from spectra in a spectra library stored generally in the DSP/CPU 9.

FIG. 13B illustrates the database calibration process. It indicates the application of the calculated calibration parameters obtained using the adaptive calibration algorithm where the error estimation (see FIG. 13A) is the input to the algorithm and the calibration parameters are the output of the algorithm. The calculated calibration parameters are used to modify measured results of the target samples being investigated. Each data point is modified in two dimensions according to the relevant calibration parameters, thus compensating for system instabilities and deficiencies. A calibration parameter is separately calculated for each laser in the array. Note that the calibration material need not be the same material as the target material. As long as a known spectrum or series of spectra at different known quantities/concentrations for one or more known materials is available, adaptive calibration can be used.

Method of Data Processing

FIG. 14, to which reference is now made, shows a flowchart 300 for an exemplary non-limiting description of a method of data processing which may be used to generate an SRS spectra using the spectrophotometer system described herein above.

FIG. 14 describes the data processing sequence used to generate an SRS spectrum based on a predefined number of measurement cycles.

Step 302—Set all hardware values to their initial setup.

Step 303—Measure the spectral data of the samples in detection element contain calibration sample, over a predefined range. This step is performed as described in FIG. 12 but only for the detection elements containing a calibration sample and not for those containing a target sample.

Step 304—Apply one of many known SNR improvement algorithms, utilizing the repetitive samples of each measuring point, to generate a calibration sample spectrum.

Step 305—Estimate measurement error by measuring results of the calibration sample and comparing it to expected results thus providing a two dimensional (wavelength and intensity) error value for each spectrum point. This step is shown in, and discussed in conjunction with, for example, FIG. 13A. The expected results are obtained from a library of spectra stored in the system's DSP/CPU.

Step 308—Calculate parameters for correction of the laser values based on the error estimation calculation determined in step 305.

Step 310—Calculate physical calibration values for laser hardware (HW), e.g. laser input current, thermo-electric cooler (TEC) setting, etc. Based on these calculations the pump and Stokes laser hardware (HW) settings are adjusted inter alia by adjusting power, wavelength, etc., as necessary Step 315—Measure spectral data for target sample(s) and the calibration sample(s) A possible method for making these measurements is described in conjunction with FIG. 12.

Step 316—Apply one of many known SNR improvement algorithms, utilizing the repetitive samples of each measurement point, to generate a spectrum for each target and calibration sample Step 317—Estimate measurement error. Intensity and wavelength errors are determined for the target sample results based on the measured calibration sample results and the known values from the stored spectra of the library's calibration spectra. This step is shown in, and discussed in conjunction with for example, FIG. 13A.

Step 318—Compare estimated measurement errors from step 317 to pre-defined limits. If one or more of the estimated measurement errors is above the pre-defined limits, return to Step 308 for physical calibration. If all of the errors are smaller than the predefined limits, continue to Step 320.

Step 320—Calculate error correction parameters using any of many known adaptive calibration algorithms. The error estimation parameters, from step 317, together with the previous calibration parameters are then used for calculation of the new calibration parameters.

Step 330—Perform database calibration (software only) by modifying each spectrum point of the target sample according to the error correction parameters, as determined in FIG. 13B. Each data point of each target sample is modified in two dimensions according to the relevant correction parameter.

Step 335—Provide a fully processed and calibrated SRS spectrum or calibrated spectral data for each target sample. This spectrum or calibrated spectral data may be exported for further processing or recording. For example, the spectral data of the Raman spectrum obtained may be exported for identification of the target sample by comparing the result to a Raman spectrum library.

Step 337—Check if the last predetermined cycle has been reached.

Step 338—If last cycle has not been reached, detection elements containing target samples are prepared for the next measurement cycle. For example, a new sample that may contain new materials or the same materials but with different quantities is inserted into the detection element and then proceed to Step 315.

Step 340—If last cycle has been reached in Step 337, terminate processing.

The above data processing method should be considered to be an exemplary method and it is not intended to limit the use of other data processing methods.

The HW calibration is performed prior to the measurement process. The laser diodes of the system's lasers are calibrated based on the results obtained from the calibration sample being used. This may be effected, for example, by using a thermo-electric cooler (TEC) attached to each laser diode and tuning control parameters to obtain a desired temperature. The SW adaptive calibration is performed by measuring the target samples, substantially simultaneously with the calibration sample measurement. The changes in the spectrum peak amplitudes and peak wavelengths are recorded. A weighted moving average algorithm or some other known adaptive calibration algorithm may be applied to the calibration data and used to calibrate the measured target sample results.

A person skilled in the art will readily comprehend that there are additional elements that may be part of, or in communication with, the system described above in conjunction with FIGS. 2-10. These include, but without intending to limit the invention, a power source, a temperature control unit, etc. Communication between these units and the elements and subsystems discussed above can easily be combined by persons skilled in the art and therefore no additional details are presented.

Output and/or control devices, such as, but without intending to limit the present invention, displays, printers, alarms or controllers may be in electronic communication with system server 105, In other embodiments of this invention, the results of the collected SRS spectral data can be forwarded to a controller of an operational system, the latter integrated with the SRS system discussed herein above. This integration allows for information to be forwarded directly from the system server 105 to the controller of the operational system. The information could provide real-time results inter alia indicating that the target operational system is operating under less than optimal conditions. The analysis of the received information can be used to change/modify/retune the setup of operational system to which it is connected. The result of such modification could be, without intending to limit the present invention, feedback input to ensure operation within the required limits, safety shut-down, limit alerts, or alerts as to the presence of undesirable or unexpected materials and/or materials in undesirable quantities in the target samples being analyzed. The controller of the integrated operational system could then shut down the operational system or otherwise indicate to a user that manual shut down or another corrective operation is required.

It is envisioned that the system of the present invention provides for high-resolution, real-time on-line analysis in industrial settings through continuous or periodic SRS spectrum generation. These settings may include, but without intending to limit the present invention, analysis of gas and liquids, analysis of the chemical composition of very small samples in sample streams in extreme temperature, noise, vibration, corrosive environment. These can be integrated directly with other operational systems, for example, and without intending to limit the present invention, systems used in industrial chemical processes, in air and water analysis, in toxicology detection, in laboratory and field analytical chemistry, and in medical detection. Such integration would, for example, in the case of industrial chemical processes provide on-line, real-time composition analysis of the target material(s) and enable real-time correction(s) of process conditions.

Figure 15:
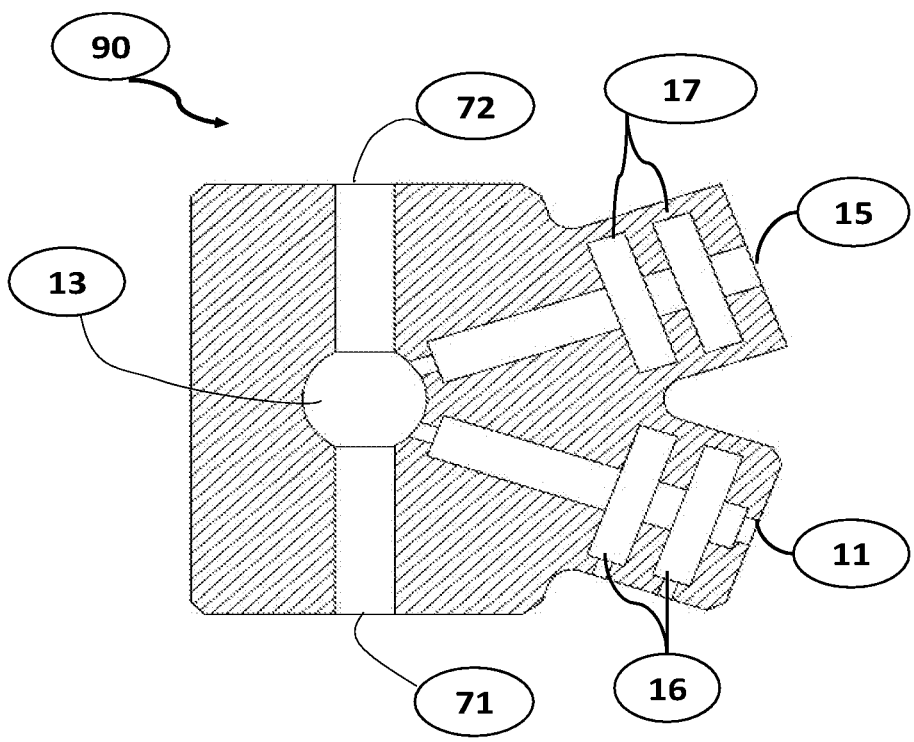
FIG. 15. is a schematic presentation of a detection element (also described in FIG. 8).

Reference is now made to FIG. 15 showing a schematic presentation of a detection element 90 also described in more simplified schematic terms in FIG. 8. A sample stream enters through sample inlet 71 into detection chamber 13 and exits through sample outlet 72. The combined pump and Stokes laser beam arrives at laser beam inlet 11 from laser sources subsystem 101 (FIG. 4) and undergoes beam concentration at focus lens 16 to a required position in detection chamber 13. The beam passes through detection chamber 13 where a stream of target material(s) are to be analyzed; further refocusing by lens 17 delivers the beam to the laser beam outlets 15 in optical communication with photodetector subsystem 103B (FIG. 10) discussed above.

Examples for industrial monitoring include: in refineries—octane calculations in petrol blending; in energy generation—WOBBE index calculations for combustion processes; in pharmaceutical manufacturing—end-of process, real-time indication of API (active pharmaceutical ingredient) generation; detection of counterfeit medication.

In another embodiment of the present invention, the system provided allows for quick accurate quantitative and qualitative analysis of chemical and biochemical materials present in microfluidic samples due to the system's high resolution and small sample required. The method of interfacing the fluids and optics in the microfluidic elements and systems within the larger envisioned system described above are known to persons skilled in the art and will not be discussed further.

It should be noted that a calibration method as described herein above may not be needed in all cases to adjust hardware settings of the system or further process the spectral data acquired by the system. Therefore the use of a calibration method requiring a calibration sample may be deemed as one specific embodiment of the envisioned system and method described herein.

It should further be noted and understood that when a single subsystem is being discussed it is to be viewed in the context of the entire system described herein. Each subsystem described is in communication and works in coordination with the other subsystems of the spectrophotometer. Without such communication/coordination, the spectrophotometer would not be able to obtain and generate spectral data and spectra of the quality it does.

Citation or identification of any reference in this application shall not be construed as an admission that such reference is available as prior art to the present invention.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A stimulated Raman scattering spectrophotometer (SRS) system comprising:
a pump laser and a Stokes laser wherein one of either said pump or said Stokes laser is a narrow range tunable laser while the other is a fixed wavelength laser array said tunable and fixed wavelength lasers adapted and configured to produce a series of combined laser beams so that only one of said fixed wavelength laser is activated at a given time and forms a combined beam with the tunable laser; a timing generator activating said tunable and fixed wavelength lasers in a predetermined sequence for generating said series of combined beams; at least one detection probe comprising at least one detection element containing a target sample in optical communication with said pump and Stokes lasers so as to be illuminated by the combined beams; at least one wavelength splitter for splitting the combined beams received from said detection elements into pump and Stokes laser beams; a plurality of photodetectors for receiving the split beams and for converting them into analog signals and then conveying them to a plurality of analog and digital convertors for conversion to digital signals; and a control and data processing subsystem for further processing the digital signals generating a SRS spectrum from the processed signals.

2. A system according to claim 1, wherein said tunable laser and fixed wavelength lasers are pulsed lasers and where said tunable laser has a pulse duration of a length such that a duration of any of said fixed wavelength laser pulses falls completely within the duration of said tunable laser pulse when both are operated together.

3. A system according to claim 1, wherein said tunable laser can be operated in a continuous scanning mode or in a discrete specific spectral peak mode.

4. A system according to claim 1, used for real-time molecular level monitoring, real-time measurement of industrial processes, real-time feedback control of these processes, temperature measurement of industrial processes for real-time molecular level monitoring, real-time measurement of environmental parameters, and detection of biomarkers in medical applications.

5. A stimulated Raman scattering spectrophotometer system comprising:
i. a laser sources subsystem comprising a pulsed pump laser and an array of pulsed Stokes lasers and one of either the pump laser or the Stokes laser array is tunable, said lasers adapted and configured to produce a series of combined laser beams;
ii. at least one detection element which contains a target sample which is illuminated by the series of combined beams;
iii. a photodetector subsystem comprising at least one wavelength splitter for splitting the combined beams received from said at least one detection element into pump and Stokes laser beams and a plurality of photodetectors adapted and configured for receiving said split beams, converting them to analog electronic signals, and then directly providing the analog signals to a plurality of analog-to-digital convertors (ADCs), while in parallel, also providing the analog electronic signals to an analog processing unit (APU), said APU configured and adapted to manipulate the analog signals in order to increase the signal-to-noise ratio (SNR) and improve resolution of the signals, the manipulated analog signals then conveyed from said APU to said plurality of ADCs where all analog signals are converted to digital signals; and iv. a control and data processing subsystem comprising a digital signal processor (DSP) and/or central processing unit (CPU) for receiving and further processing the digital signals received from said ADCs and then generating a SRS spectrum from the processed digital signals.

6. A system according to claim 5, wherein said at least one detection element comprises two detection chambers one of which contains a reference sample and the other contains said target sample.

7. A system according to claim 6 where said detection element further comprises an intensity beam splitter, said intensity beam splitter configured for splitting the intensity of said combined beam into a first portion and a second portion wherein said first portion of the split beam is directed to pass through said reference sample and said second portion of the split beam is directed to pass through said target sample.

8. A system according to claim 6, where at least two photodetectors convert the pump laser beam and the Stokes laser beam of the target sample to analog signals while at least two other photodetectors convert the pump laser beam and the Stokes laser beam of the reference sample to analog signals.

9. A system according to claim 6, wherein said DSP and/or said CPU is adapted to receive and process said target and reference sample digital signals from said ADCs and use the reference sample digital signals as background information for the target sample digital signals, said processed reference sample digital signals being subtracted from said target sample digital signals reducing noise and further increasing resolution and enhancing SNR of the target signal.

10. A system according to claim 6, wherein said APU comprises an analog circuit configured for real-time processing of the analog electronic signals of said associated target and reference samples in each of said at least one detection element, said reference signals representing background signals for subtraction in the APU from said analog signals of said target samples thus increasing resolution and enhancing SNR of the target signal.

11. A system according to claim 5, wherein the pump laser pulse duration is longer than the Stokes laser pulse duration, so that for a portion of the time during the pulse of said pump laser the target sample is illuminated by said pump laser without the Stokes laser illuminating the target sample while for the remainder of the pump laser pulse duration both pump and Stokes lasers illuminate the target sample.

12. A system according to claim 5, wherein said APU comprises an analog circuit configured for real-time processing of the analog signals and where the pump signal is delayed using a delay line so that the pump signal from the time said pump laser is illuminated while said Stokes laser is not serves as a reference signal representing background signals which are subtracted from said target signal of said pump laser illuminated in combination with said Stokes laser, thus increasing the resolution and enhancing the SNR of the target signal.

13. A system according to claim 5, where said target sample in said detection element is a stream of target material(s) that is to be analyzed.

14. A stimulated Raman scattering spectrophotometer system comprising:

a. a laser sources subsystem comprising a pulsed pump laser and an array of pulsed Stokes lasers and one of either the pump laser or the Stokes laser array is tunable, said lasers configured to produce a series of combined laser beams;

b. at least one detection element wherein at least one detection chamber includes a target sample and at least one detection chamber includes a calibration sample, said at least two detection chambers are illuminated sequentially by the combined laser beams;

c. at least one wavelength splitter for splitting the combined beams received from said at least two detection chambers into pump and Stokes laser beams and a plurality of photo-detectors for converting said pump and Stokes beams into analog signals which are then converted to digital signals by ADCs; and d. a control and data processing subsystem for further processing and calibrating the digital signals and for generating a SRS spectrum from the processed signals.

15. A system according to claim 14, wherein the Stokes lasers and pump laser comprise unstable lasers with large impairments.

16. A method for improving the accuracy of a stimulated Raman scattering (SRS) spectrum of a target sample generated by a SRS spectrophotometer system as defined in claim 14, the method comprising the steps of:

a. generating a SRS spectrum of the calibration sample;

b. estimating measurement errors by comparing the measured calibration sample spectrum with a series of spectra for different known quantities of the known calibration material(s) in the calibration sample;

c. if the measurement errors are equal to or exceed predefined values, calibrating the physical parameters of the laser sources and repeating step i and ii;

d. if the measurement errors are less than predefined values, calculating calibration parameters using the estimated measurement errors;

e. generating a SRS spectrum of one or more target sample(s);

f. modifying the SRS spectrum of each target sample using the calibration parameters; and g. conveying the modified target spectrum to an output device or control device for control of an operational system.

17. The method according to claim 16, wherein said step of estimating measurement errors and calculating calibration parameters, each measurement error and calibration parameter is a two-dimensional value: wavelength error/parameter and intensity error/parameter.

18. The method according to claim 16, if there is continuous or periodic SRS spectrum generation, said step of estimating measurement errors, uses a combination of current and prior estimated error measurements employing a known adaptive calibration method.

* * * * *